US010188330B1

(12) United States Patent
Kadlec et al.

(10) Patent No.: US 10,188,330 B1
(45) Date of Patent: Jan. 29, 2019

(54) METHODS AND SYSTEMS FOR DETERMINING A LIGHT DRIVE PARAMETER LIMIT IN A PHYSIOLOGICAL MONITOR

(71) Applicant: Covidien LP, Mansfield, MA (US)

(72) Inventors: Ron Kadlec, Longmont, CO (US); John Mackinnon, Edinburgh (GB); Greg Lund, Boulder, CO (US); Andy Lin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 893 days.

(21) Appl. No.: 14/614,274

(22) Filed: Feb. 4, 2015

Related U.S. Application Data

(60) Provisional application No. 61/936,197, filed on Feb. 5, 2014.

(51) Int. Cl.
| | |
|---|---|
| *A61B 5/1455* | (2006.01) |
| *H05B 37/02* | (2006.01) |
| *H05B 33/08* | (2006.01) |
| *A61B 5/0205* | (2006.01) |
| *A61B 5/1495* | (2006.01) |
| *A61B 5/00* | (2006.01) |
| *A61B 5/024* | (2006.01) |

(52) U.S. Cl.
CPC ........ *A61B 5/14552* (2013.01); *A61B 5/0205* (2013.01); *A61B 5/1495* (2013.01); *A61B 5/7221* (2013.01); *A61B 5/7246* (2013.01); *A61B 5/7264* (2013.01); *H05B 33/0803* (2013.01); *H05B 37/02* (2013.01); *A61B 5/02405* (2013.01); *A61B 5/02427* (2013.01)

(58) Field of Classification Search
CPC . A61B 5/1455; A61B 5/14551; A61B 5/7221; A61B 5/7257; A61B 2560/0204; A61B 2560/0209
See application file for complete search history.

(56) References Cited

U.S. PATENT DOCUMENTS

| | | |
|---|---|---|
| 4,942,877 A | 7/1990 | Sakai et al. |
| 5,457,790 A | 10/1995 | Iwamura et al. |
| 5,645,068 A | 7/1997 | Mezack et al. |
| 5,657,215 A | 8/1997 | Faulk |
| 5,778,882 A | 7/1998 | Raymond et al. |
| 5,792,052 A | 8/1998 | Isaacson et al. |

(Continued)

OTHER PUBLICATIONS

Allen, J., "Photoplethysmography and its Application in Clinical Physiological Measurement," Physiol. Meas., vol. 28, Mar. 2007, pp. R1-R39.

(Continued)

*Primary Examiner* — Eric Winakur

(57) ABSTRACT

A physiological monitoring system may receive a sensor signal from a physiological sensor. The system may determine a parameter based on the sensor signal, for example variability of a blood oxygen saturation value or the percent modulation of a light signal. The system may determine a light drive parameter limit based on one or more parameters. For example, the system may determine a light drive current limit. The frequency of changes in the limit may be regulated using a state machine and other techniques that include hysteresis. An extant light drive parameter may be updated or changed in accordance with the light drive parameter limit and a light drive signal may be generated based on the light drive parameter.

22 Claims, 12 Drawing Sheets

(56) References Cited

U.S. PATENT DOCUMENTS

| | | | |
|---|---|---|---|
| 6,147,618 | A | 11/2000 | Halleck et al. |
| 6,351,658 | B1 | 2/2002 | Middleman et al. |
| 6,356,774 | B1 | 3/2002 | Bernstein et al. |
| 6,377,185 | B1 | 4/2002 | Halleck et al. |
| 6,515,273 | B2 | 2/2003 | Al-Ali |
| 6,697,658 | B2 | 2/2004 | Al-Ali |
| 6,697,665 | B1 | 2/2004 | Rava et al. |
| 6,731,967 | B1 | 5/2004 | Turcott |
| 6,734,802 | B2 | 5/2004 | Halleck et al. |
| 6,863,652 | B2 | 3/2005 | Huang et al. |
| 7,162,288 | B2 | 1/2007 | Nordstrom et al. |
| 7,295,866 | B2 | 11/2007 | Al-Ali |
| 7,333,541 | B2 | 2/2008 | Min et al. |
| 7,382,247 | B2 | 6/2008 | Welch et al. |
| 7,486,386 | B1 | 2/2009 | Holcombe et al. |
| 7,499,740 | B2 | 3/2009 | Nordstrom et al. |
| 7,541,790 | B2 | 6/2009 | Schopfer et al. |
| 7,630,078 | B1 | 12/2009 | Nabutovsky et al. |
| 7,831,011 | B2 | 11/2010 | Ayala et al. |
| 7,841,985 | B2 | 11/2010 | Hicks |
| 7,843,978 | B2 | 11/2010 | Souhaite et al. |
| 7,889,069 | B2 | 2/2011 | Fifolt et al. |
| 7,996,187 | B2 | 8/2011 | Nanikashvili et al. |
| 8,078,248 | B2 | 12/2011 | Lee et al. |
| 8,116,837 | B2 | 2/2012 | Huang |
| 8,145,287 | B2 | 3/2012 | Diab et al. |
| 2003/0028085 | A1 | 2/2003 | Al-Ali |
| 2004/0002637 | A1 | 1/2004 | Huang et al. |
| 2004/0116969 | A1 | 6/2004 | Owen et al. |
| 2004/0225225 | A1 | 11/2004 | Naumov et al. |
| 2005/0187446 | A1 | 8/2005 | Nordstrom et al. |
| 2006/0178588 | A1 | 8/2006 | Brody |
| 2007/0038049 | A1 | 2/2007 | Huang |
| 2007/0055163 | A1 | 3/2007 | Asada et al. |
| 2007/0208236 | A1 | 9/2007 | Hicks |
| 2008/0086440 | A1 | 4/2008 | Hoey et al. |
| 2008/0108887 | A1 | 5/2008 | Higgins |
| 2008/0161663 | A1 | 7/2008 | Lee et al. |
| 2008/0208273 | A1 | 8/2008 | Owen et al. |
| 2008/0278336 | A1 | 11/2008 | Ortega et al. |
| 2008/0319290 | A1 | 12/2008 | Mao et al. |
| 2009/0247846 | A1 | 10/2009 | Rantala |
| 2009/0247849 | A1 | 10/2009 | McCutcheon et al. |
| 2009/0259116 | A1 | 10/2009 | Wasserman et al. |
| 2009/0270703 | A1 | 10/2009 | Diab et al. |
| 2010/0056887 | A1 | 3/2010 | Kimura et al. |
| 2010/0128838 | A1 | 5/2010 | Ayala et al. |
| 2010/0234718 | A1 | 9/2010 | Sampath et al. |
| 2010/0317937 | A1 | 12/2010 | Kuhn et al. |
| 2011/0004081 | A1 | 1/2011 | Addison et al. |
| 2011/0028854 | A1 | 2/2011 | Addison et al. |
| 2011/0071406 | A1 | 3/2011 | Addison et al. |
| 2012/0004519 | A1 | 1/2012 | Nazarian et al. |
| 2012/0035485 | A1 | 2/2012 | Owen et al. |
| 2012/0116193 | A1 | 5/2012 | Huang |
| 2012/0184830 | A1 | 7/2012 | Balberg et al. |
| 2012/0232354 | A1 | 9/2012 | Ecker et al. |

OTHER PUBLICATIONS

Murray, W. B., and Foster, P. A., "The Peripheral Pulse Wave: Information Overlooked," J. Clin. Monit., vol. 12, Sep. 1996, pp. 365-377.

Shelley, K. H., "Photoplethysmography: Beyond the Calculation of Arterial Oxygen Saturation and Heart Rate," Anesth. Analg., vol. 105, Dec. 2007, pp. S31-S36.

METHODS AND SYSTEMS FOR DETERMINING A LIGHT DRIVE PARAMETER LIMIT IN A PHYSIOLOGICAL MONITOR

CROSS REFERENCE TO RELATED APPLICATION

This application claims the benefit of U.S. Provisional Application No. 61/936,197, filed Feb. 5, 2014, which is hereby incorporated by reference herein in its entirety.

SUMMARY

The present disclosure relates to processing and generating signals in a physiological monitor, and more particularly relates to determining a light drive parameter limit based on a signal received by a pulse oximeter or other medical device.

The present disclosure is directed towards the processing and generating of signals in a physiological monitoring system such as a medical device. Methods and systems are provided for determining a light drive parameter limit based on a received signal. In some embodiments, light signals are received by a system. The system determines one or more parameters based on the received signals. For example, determined parameters may include light signal intensity, light signal variability, physiological parameters such as pulse rate or blood oxygen saturation, and other parameters. The system may determine if the one or more parameters are within a desired range, and may combine those decisions using a logical operation. The outcome of the logical operation may be used to operate a state machine that regulates a light drive parameter limit. An extant light drive parameter may be compared with the limit, and the light drive parameter may be updated based on the comparison. A light signal may be generated based on the light drive parameter and provided to a subject. An attenuated light signal corresponding to the generated light signal may be received and may be used to determine a physiological parameter of the subject. Physiological parameters may include, for example, pulse rate and blood oxygen saturation.

In some embodiments, a method is provided for driving a medical sensor for use on a subject. The method comprises generating, using processing equipment, a light drive signal in accordance with a maximum current limit, where the light drive signal is configured to produce an emitted light in the medical sensor. The method further comprises receiving a sensor signal from the medical sensor, in response to the emitted light. The method further comprises determining a parameter based on the received sensor signal and changing the maximum current limit based on the parameter. The method further comprises generating the light drive signal in accordance with the changed maximum current limit.

In some embodiments, a system is provided for driving a medical sensor for use on a subject. The system comprises processing equipment configured to perform operations. The operations comprise generating a light drive signal in accordance with a maximum current limit, where the light drive signal is configured to produce an emitted light in the medical sensor. The operations further comprise receiving a sensor signal from the medical sensor, in response to the emitted light. The operations further comprise determining a parameter based on the received sensor signal and changing the maximum current limit based on the parameter. The operations further comprise generating the light drive signal in accordance with the changed maximum current limit.

In some embodiments, a method is provided for monitoring a physiological parameter of a subject. The method comprises driving, using processing equipment, a medical sensor to emit light into a subject and receiving a sensor signal from the medical sensor in response to the emitted light. The method further comprises determining a plurality of parameters based on the sensor signal and comparing each of the plurality of parameters to a respective threshold or condition. The method further comprises determining, for each of the plurality of parameters, a vote based on whether the parameter meets its respective threshold or condition. The method further comprises combining the votes of the plurality of parameters and reducing the maximum current available to the medical sensor based on the combined votes. The method further comprises driving the medical sensor in accordance with the reduced maximum current.

In some embodiments, a system is provided for monitoring a physiological parameter of a subject. The system comprises processing equipment configured to perform operations. The operations comprise driving a medical sensor to emit light into a subject and receiving a sensor signal from the medical sensor in response to the emitted light. The operations further comprise determining a plurality of parameters based on the sensor signal and comparing each of the plurality of parameters to a respective threshold or condition. The operations further comprise determining, for each of the plurality of parameters, a vote based on whether the parameter meets its respective threshold or condition. The operations further comprise combining the votes of the plurality of parameters and reducing the maximum current available to the medical sensor based on the combined votes. The operations further comprise driving the medical sensor in accordance with the reduced maximum current.

In some embodiments, a method is provided for generating a light drive signal. The method comprises receiving, using processing equipment, a sensor signal. The method further comprises determining at least one parameter based on the received sensor signal. The method further comprises determining a light drive parameter limit based on the at least one parameter and comparing an extant light drive parameter to the light drive parameter limit. The method further comprises adjusting, based on the comparison, the extant light drive parameter. The method further comprises generating a light drive signal based on the adjusted light drive parameter.

In some embodiments, a system is provided for generating a light drive signal. The system comprises processing equipment configured to perform operations. The operations comprise receiving a sensor signal. The operations further comprise determining at least one parameter based on the received sensor signal. The operations further comprise determining a light drive parameter limit based on the at least one parameter and comparing an extant light drive parameter to the light drive parameter limit. The operations further comprise adjusting, based on the comparison, the extant light drive parameter. The operations further comprise generating a light drive signal based on the adjusted light drive parameter.

In some embodiments, a method and system are provided for determining whether to enable the adjustment of a parameter setting (e.g., a light drive parameter limit) based on a sensor setting and a monitor setting. In some embodiments, a method and system are provided for displaying status information related to the status of a light drive parameter limit.

BRIEF DESCRIPTION OF THE FIGURES

The above and other features of the present disclosure, its nature and various advantages will be more apparent upon consideration of the following detailed description, taken in conjunction with the accompanying drawings in which.

DETAILED DESCRIPTION OF THE FIGURES

Figure 1:
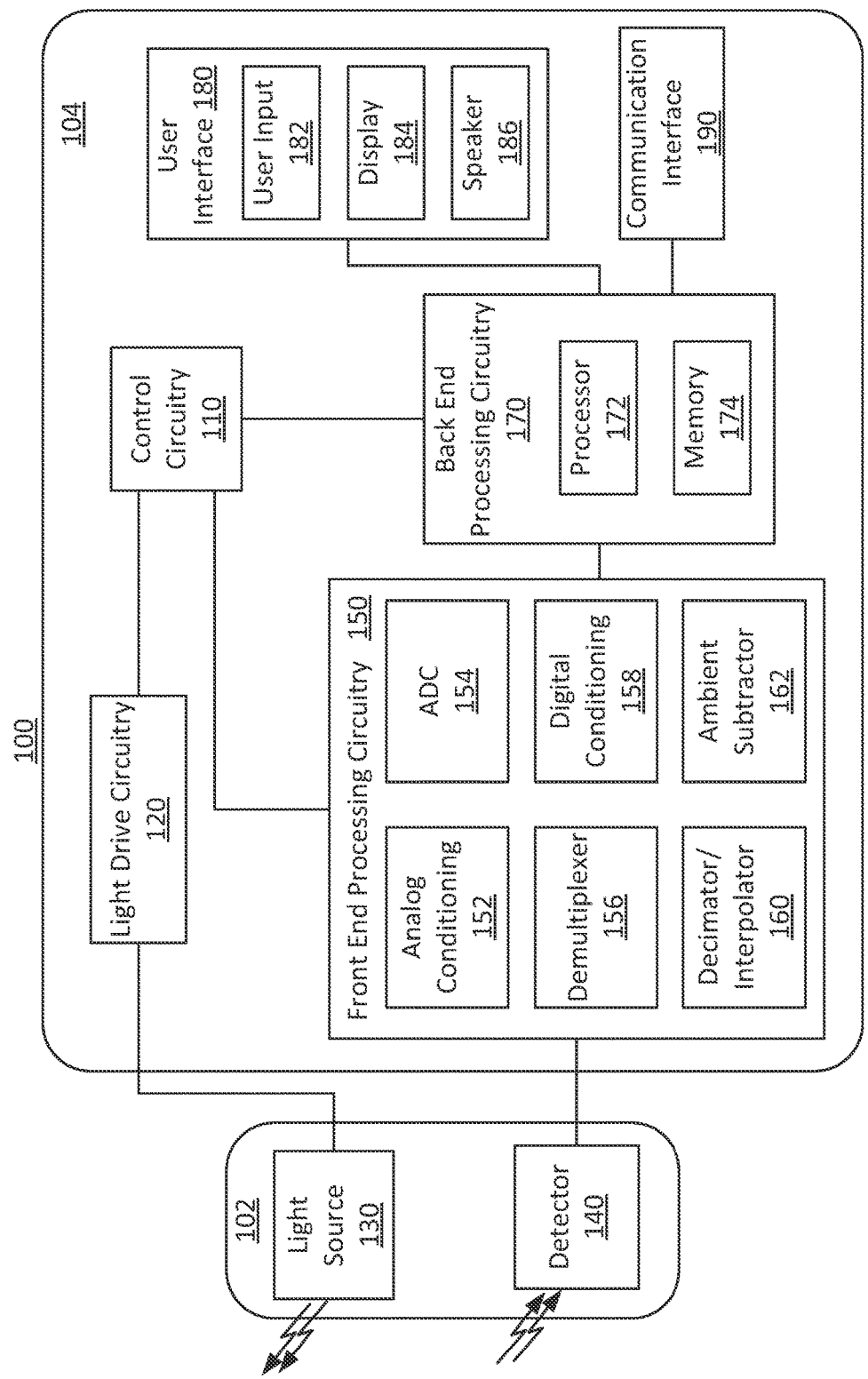
FIG. 1 shows a block diagram of an illustrative physiological monitoring system in accordance with some embodiments of the present disclosure.

The present disclosure is directed towards the processing and generating of signals in a physiological monitoring system such as a medical device. In an embodiment, a medical device includes a light emitter for emitting light into a subject, and a drive signal that causes light to be emitted from the light emitter. In order to reduce the power consumed by the medical device, a system is provided to determine a limit to be applied to a parameter of the light drive signal. For example, in an embodiment, the parameter of the light drive signal is a current of the signal, and a limit applied to the parameter is a maximum current limit. In order to reduce power consumed by the medical device, the maximum current limit may be changed, based on an analysis of one or more parameters. In some embodiments, power is reduced by determining or adjusting a system operating parameter that affects the amount of power consumed by the medical device.

In some embodiments, a signal is received from the medical device, in response to the emitted light. The received sensor signal may be processed to determine one or more parameters. Parameters may include signal parameters such as signal modulation and signal amplitude. Parameters may also include physiological parameters determined based on the received signal, such as pulse rate and oxygen saturation (e.g., $SpO_2$). Parameters may also include system parameters such as a sensor-off condition. The system may process the parameters to determine, for example, if they are in a particular desired range. For example, the system may determine if a pulse rate is in a low, acceptable, or high range. The results of the parameter processing may be combined using a logical operation, and the result of that logical operation may be used to determine or update the light drive parameter limit.

For example, in an embodiment, the light drive parameter is a current of the light drive signal, and the light drive parameter limit may include a maximum current ($I_{max}$). The maximum current $I_{max}$ sets a maximum current to be used by the medical sensor, such as by light emitters associated with a pulse oximeter sensor. Based on one or more parameters from the received sensor signal, described above, the system determines whether to change $I_{max}$. It will be understood that when $I_{max}$ is imposed as a current limit, the pulse oximeter may use an emitter current that is less than $I_{max}$. In some embodiments, an extant light drive parameter (e.g., an existing current) may be compared to the light drive parameter limit, and the extant light drive parameter may be updated based on that comparison. For example, where the light drive parameter limit is $I_{max}$, if $I_{max}$ is reduced and the extant light drive current is higher than the new $I_{max}$, the light drive current may be decreased to a value less than or equal to $I_{max}$. Light drive parameters may additionally or alternatively include light drive pulse shaping, duty cycle, selection of a light drive algorithm, selection of light emitters, gain level, brightness, any other suitable parameters, or any combination thereof. Light drive parameter limits corresponding to these light drive parameters may be determined.

In some embodiments, the light drive parameter limit may be adjusted in order to save power, when possible and/or desired. For example, $I_{max}$ may be used as the light drive parameter limit, in order to control the amount of power available to the light emitters of the sensor. The $I_{max}$, and thus the amount of available power, may be reduced when a subject shows healthy vital signs, while the amount of available power may be increased when vital signs decrease and the accuracy of the calculation of physiological information takes priority over saving power. Available power may also be increased when signal quality is diminished, and/or decreased when signal quality is improved.

Increasing an amount of current provided to light emitters may increase the signal strength of a received signal. It may be possible to reduce the power provided to the emitters and still receive a signal of high enough amplitude and quality to reliably determine physiological parameters or other outputs. In some embodiments, one or more determined physiological parameters may be used in determining light drive parameter limits and/or light drive parameters. For example, if all of the determined physiological parameters are in acceptable ranges, the $I_{max}$ limit may be decreased, or may remain at a decreased level, in order to decrease the available power to the emitters, and thus potentially decrease power consumption. If, however, one or more parameters are not in an acceptable range, then the $I_{max}$ limit may be increased, or may remain at an increased level. It will be understood that the parameter limit decision may include physiological parameters (e.g., $SpO_2$), signal parameters (e.g., received signal amplitude), system parameters (e.g., probe-off conditions), any other suitable parameters, or any combination thereof.

It will be understood that increasing a parameter limit need not, but may, correspond to changing a parameter. In some embodiments, a parameter limit may correspond to an available range of settings for a parameter, and the system may determine a parameter within that range based on other considerations. For example, if an upper limit is updated such that an extant parameter exceeds the range, the parameter may be updated so that it falls within the range. If an upper limit is updated such that the extant parameter is still within the range, the parameter may remain unchanged. For example, where the parameter limit is $I_{max}$, the system may adjust the current I to any suitable value within the limit based on any suitable techniques, for example based on a signal quality metric. In an example, when $I_{max}$ is increased, the extant parameter I may still be below the limit, but the normal adjustment processing for I may concurrently or subsequently increase current as a result of the higher limit. If the adjustment processing for I includes a signal quality metric, the signal quality may be low when the $I_{max}$ limit increases. Therefore, it is possible that I will also rise to a higher level when the $I_{max}$ limit increases.

In some embodiments, more than one light drive parameter may be determined. The limits may be determined based on one or more light drive parameters. In an example, a pulse oximeter may have a red light source and an IR light source. Light drive parameters limits and light drive parameters may be updated for the red and IR sources together, independently, relative to one another, by any other suitable technique, or any combination thereof.

As used herein, percent modulation of a sensor signal refers to the size of the varying portion of the signal with respect to the constant portion of the signal. For example, the percent modulation may relate to the amount of the pulsatile portion of a signal with respect to the non-pulsatile portion. In another example, percent modulation may relate to an AC/DC (alternating component/direct component) ratio. In some embodiments, percent modulation may refer to the percent modulation of a demultiplexed signal. For example, an alternative red and IR light pattern may be received at a light detector. This signal may be demultiplexed to generate a red light signal and an IR light signal. A percent modulation may be determined for the red signal, the IR signal, the combined signal, any other suitable signal, or any combination thereof.

As used herein, nAv corresponds to a virtual nanoamp signal that represents the amount of light transmitted through a subject, which may be measured as the amount of light received at a detector. For example, an optical detector in a pulse oximeter may use a photodetector to receive a light signal after an emitted light signal has been partially attenuated by interaction with a subject. The amount of received light may be represented as current in an electrical signal. The nAv signal is a virtual signal that corresponds to that detected signal. The virtual signal may include corrections, for example those relating to demultiplexing, gain stages, filters, and other signal processing techniques, such that the nAv signal represents the amount of transmitted light. In some embodiments, nAv may represent the signal strength or amplitude of a received signal.

As used herein, hysteresis refers to a process that considers both the extant situation and historical information in establishing a new state. For example, a system may change from a first state to a second state only if a parameter has remained above a threshold for a particular amount of time. In another example, a system may have a first threshold to change from a low to high state, and a second threshold to change from a high to low state, where the first and second thresholds differ.

In some embodiments, hysteresis and other techniques may be used to reduce the frequency of system state toggling and other changes. It may be desirable to reduce toggling in order to increase system stability, reduce electronic noise associated with switching, reduce artifacts, reduce power consumption, for any other suitable reason, or any combination thereof. In an example, when a metric used to select a state is close to a simple, non-hysteretic threshold, the system may rapidly toggle between two states. At each switch, the system may require adjustment of light output currents, amplification stages, calibration, and other steps that include increased processing load and/or signal noise. By including hysteresis, the rapid switching is reduced or avoided. In an example, switching between states may require a finite amount of subsequent settling time in order to achieve a reliable output.

As used herein, a state machine refers to a processing technique where multiple states are defined, as well as the parameters for transitioning between states. Generally, a system exists in one state at any given time, and transitions to another state based on the extant and prior conditions. State machines may inherently include hysteresis, for example in that the conditions to transition from state A to state B are not necessarily the same as the conditions required to transition from state B to state A. In an example, a state machine in a pulse oximeter may include a high available power state and a low available power state, and may transition between those states when the received signals meet particular thresholds or conditions.

As used herein, extant refers to the condition or setting that exists at that particular time. For example, the extant light drive parameter may be the value of the light drive parameter that is being used by the system at that instance.

The foregoing techniques may be implemented in an oximeter. An oximeter is a medical device that may determine the oxygen saturation of an analyzed tissue. One common type of oximeter is a pulse oximeter, which may non-invasively measure the oxygen saturation of a patient's blood (as opposed to measuring oxygen saturation invasively by analyzing a blood sample taken from the patient). Pulse oximeters may be included in patient monitoring systems that measure and display various blood flow characteristics including, but not limited to, the blood oxygen saturation (e.g., arterial, venous, or both). Such patient monitoring systems may also measure and display additional or alternative physiological parameters such as pulse rate, respiration rate, respiration effort, blood pressure, hemoglobin concentration (e.g., oxygenated, deoxygenated, and/or total), any other suitable physiological parameters, or any combination thereof. Exemplary embodiments of determining respiration rate are disclosed in Addison et al. U.S. Patent Publication No. 2011/0071406, published Mar. 24, 2011, which is hereby incorporated by reference herein in its entirety. Exemplary embodiments of determining respiration effort are disclosed in Addison et al. U.S. Patent Publication No. 2011/0004081, published Jan. 6, 2011, which is hereby incorporated by reference herein in its entirety. Exemplary embodiments of determining blood pressure are disclosed in Addison et al. U.S. Patent Publication No. 2011/0028854, published Feb. 3, 2011, which is hereby incorporated by reference herein in its entirety.

Pulse oximetry may be implemented using a photoplethysmograph. Pulse oximeters and other photoplethysmograph devices may also be used to determine other physiological parameter and information as disclosed in: J. Allen, "Photoplethysmography and its application in clinical physiological measurement," *Physiol. Meas.*, vol. 28, pp. R1-R39, March 2007; W. B. Murray and P. A. Foster, "The peripheral pulse wave: information overlooked," *J. Clin. Monit.*, vol. 12, pp. 365-377, September 1996; and K. H. Shelley, "Photoplethysmography: beyond the calculation of arterial oxygen saturation and heart rate," *Anesth. Analg.*, vol. 105, pp. S31-S36, December 2007; all of which are incorporated by reference herein in their entireties.

An oximeter may include a light sensor that is placed at a site on a patient, typically a fingertip, toe, forehead or earlobe, or in the case of a neonate, across a foot or hand. The oximeter may use a light source to pass light through blood perfused tissue and photoelectrically sense the absorption of the light in the tissue. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, around or in front of the ear, and locations with strong pulsatile arterial flow. Suitable sensors for these locations may include sensors that detect reflected light.

The oximeter may measure the intensity of light that is received at the light sensor as a function of time. The oximeter may also include sensors at multiple locations. A signal representing light intensity versus time or a mathematical manipulation of this signal (e.g., a scaled version thereof, a log taken thereof, a scaled version of a log taken thereof, an inverted signal, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate any of a number of physiological parameters, including an amount of a blood constituent (e.g., oxyhemoglobin) being measured as well as a pulse rate and when each individual pulse occurs.

In some embodiments, the photonic signal interacting with the tissue is of one or more wavelengths that are attenuated by the blood in an amount representative of the blood constituent concentration. Red and infrared (IR) wavelengths may be used because it has been observed that highly oxygenated blood will absorb relatively less red light and more IR light than blood with a lower oxygen saturation. By comparing the intensities of two wavelengths at different points in the pulse cycle, it is possible to estimate the blood oxygen saturation of hemoglobin in arterial blood.

The system may process data to determine physiological parameters using techniques well known in the art. For example, the system may determine blood oxygen saturation using two wavelengths of light and a ratio-of-ratios calculation. The system also may identify pulses and determine pulse amplitude, respiration, blood pressure, other suitable parameters, or any combination thereof, using any suitable calculation techniques. In some embodiments, the system may use information from external sources (e.g., tabulated data, secondary sensor devices) to determine physiological parameters.

In some embodiments, a light drive modulation may be used. For example, a first light source may be turned on for a first drive pulse, followed by an off period, followed by a second light source for a second drive pulse, followed by an off period. The first and second drive pulses may be used to determine physiological parameters. The off periods may be used to detect ambient signal levels, reduce overlap of the light drive pulses, allow time for light sources to stabilize, allow time for detected light signals to stabilize or settle, reduce heating effects, reduce power consumption, for any other suitable reason, or any combination thereof.

It will be understood that the techniques described herein are not limited to pulse oximeters and may be applied to any suitable medical and non-medical devices. For example, the system may determine light drive and other system parameters for use in determining physiological parameters such as regional saturation ($rSO_2$), respiration rate, respiration effort, continuous non-invasive blood pressure, oxygen saturation pattern detection, fluid responsiveness, cardiac output, any other suitable physiological parameter, or any combination thereof.

The following description and accompanying FIGS. 1-14 provide additional details and features of some embodiments of the present disclosure.

FIG. 1 shows a block diagram of illustrative physiological monitoring system 100 in accordance with some embodiments of the present disclosure. System 100 may include a sensor 102 and a monitor 104 for generating and processing sensor signals that include physiological information of a subject. In some embodiments, sensor 102 and monitor 104 may be part of an oximeter.

Sensor 102 of physiological monitoring system 100 may include light source 130 and detector 140. Light source 130 may be configured to emit photonic signals having one or more wavelengths of light (e.g. red and IR) into a subject's tissue. For example, light source 130 may include a red light emitting light source and an IR light emitting light source, e.g. red and IR light emitting diodes (LEDs), for emitting light into the tissue of a subject to generate sensor signals that include physiological information. In one embodiment, the red wavelength may be between about 600 nm and about 750 nm, and the IR wavelength may be between about 800 nm and about 1000 nm. It will be understood that light source 130 may include any number of light sources with any suitable characteristics. In embodiments where an array of sensors is used in place of single sensor 102, each sensor may be configured to emit a single wavelength. For example, a first sensor may emit only a red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 140 may be chosen to be specifically sensitive to the chosen targeted energy spectrum of light source 130.

In some embodiments, detector 140 may be configured to detect the intensity of light at the red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 140. After converting the received light to an electrical signal, detector 140 may send the detection signal to monitor 104, where the detection signal may be processed and physiological parameters may be determined (e.g., based on the absorption of the red and IR wavelengths in the subject's tissue). In some embodiments, the detection signal may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate a light drive signal, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 120, as discussed above, may be configured to generate a light drive signal that is provided to light source 130 of sensor 102. The light drive signal may, for example, control the intensity of light source 130 and the timing of when light source 130 is turned on and off. In some embodiments, light drive circuitry 120 may comprise a power supply and a switch for selectively applying power to light source 130. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

In some embodiments, control circuitry 110 and light drive circuitry 120 may generate light drive parameters based on a metric. For example, back end processing 170 may receive information about received light signals, determine light drive parameters based on that information, and send corresponding information to control circuitry 110.

Figure 2A:
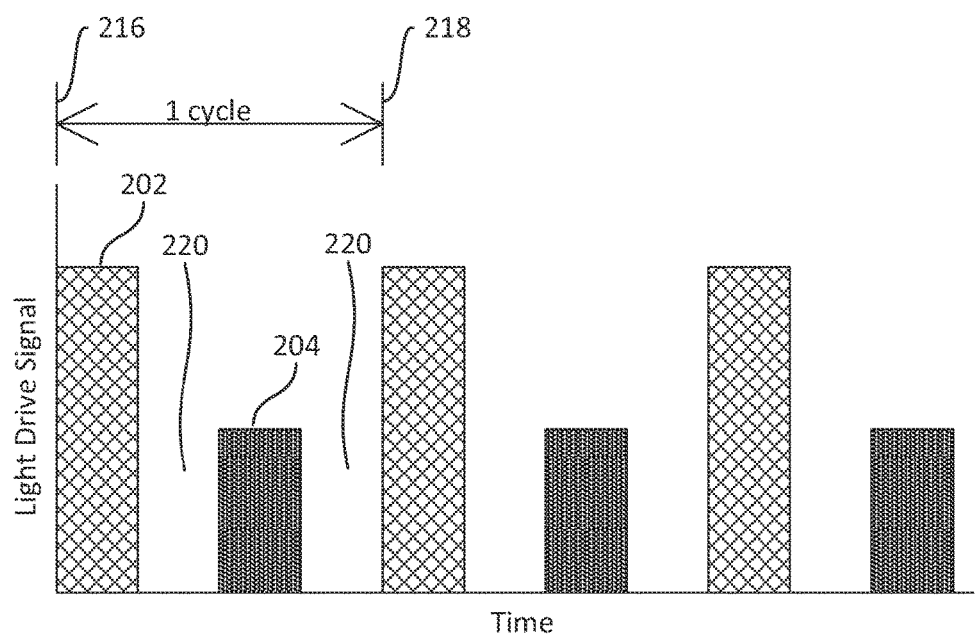
FIG. 2A shows an illustrative plot of a light drive signal in accordance with some embodiments of the present disclosure.

FIG. 2A shows an illustrative plot of a light drive signal including red light drive pulse 202 and IR light drive pulse 204 in accordance with some embodiments of the present disclosure. Light drive pulses 202 and 204 are illustrated as square waves. These pulses may include shaped waveforms rather than a square wave. The shape of the pulses may be generated by a digital signal generator, digital filters, analog filters, any other suitable equipment, or any combination thereof. For example, light drive pulses 202 and 204 may be generated by light drive circuitry 120 under the control of control circuitry 110. As used herein, drive pulses may refer to the high and low states of a shaped pulse, switching power or other components on and off, high and low output states, high and low values within a continuous modulation, other suitable relatively distinct states, or any combination thereof. The light drive signal may be provided to light source 130, including red light drive pulse 202 and IR light drive pulse 204 to drive red and IR light emitters, respectively, within light source 130. Red light drive pulse 202 may have a higher amplitude than IR light drive pulse 204 since red LEDs may be less efficient than IR LEDs at converting electrical energy into light energy. In some embodiments, the output levels may be equal, may be adjusted for nonlinearity of emitters, may be modulated in any other suitable technique, or any combination thereof. Additionally, red light may be absorbed and scattered more than IR light when passing through perfused tissue.

When the red and IR light sources are driven in this manner they emit pulses of light at their respective wavelengths into the tissue of a subject in order generate sensor signals that include physiological information that physiological monitoring system 100 may process to calculate physiological parameters. It will be understood that the light drive amplitudes of FIG. 2A are merely exemplary and that any suitable amplitudes or combination of amplitudes may be used, and may be based on the light sources, the subject tissue, the determined physiological parameter, modulation techniques, power sources, any other suitable criteria, or any combination thereof.

The light drive signal of FIG. 2A may also include "off" periods 220 between the red and IR light drive pulse. "Off" periods 220 are periods during which no drive current may be applied to light source 130. "Off" periods 220 may be provided, for example, to prevent overlap of the emitted light, since light source 130 may require time to turn completely on and completely off. The period from time 216 to time 218 may be referred to as a drive cycle, which includes four segments: a red light drive pulse 202, followed by an "off" period 220, followed by an IR light drive pulse 204, and followed by an "off" period 220. After time 218, the drive cycle may be repeated (e.g., as long as a light drive signal is provided to light source 130). It will be understood that the starting point of the drive cycle is merely illustrative and that the drive cycle can start at any location within FIG. 2A, provided the cycle spans two drive pulses and two "off" periods. Thus, each red light drive pulse 202 and each IR light drive pulse 204 may be understood to be surrounded by two "off" periods 220. "Off" periods may also be referred to as dark periods, in that the emitters are dark or returning to dark during that period. It will be understood that the particular square pulses illustrated in FIG. 2A are merely exemplary and that any suitable light drive scheme is possible. For example, light drive schemes may include shaped pulses, sinusoidal modulations, time division multiplexing other than as shown, frequency division multiplexing, phase division multiplexing, any other suitable light drive scheme, or any combination thereof.

Referring back to FIG. 1, front end processing circuitry 150 may receive a detection signal from detector 140 and provide one or more processed signals to back end processing circuitry 170. The term "detection signal," as used herein, may refer to any of the signals generated within front end processing circuitry 150 as it processes the output signal of detector 140. Front end processing circuitry 150 may perform various analog and digital processing of the detector signal. One suitable detector signal that may be received by front end processing circuitry 150 is shown in FIG. 2B.

Figure 2B:
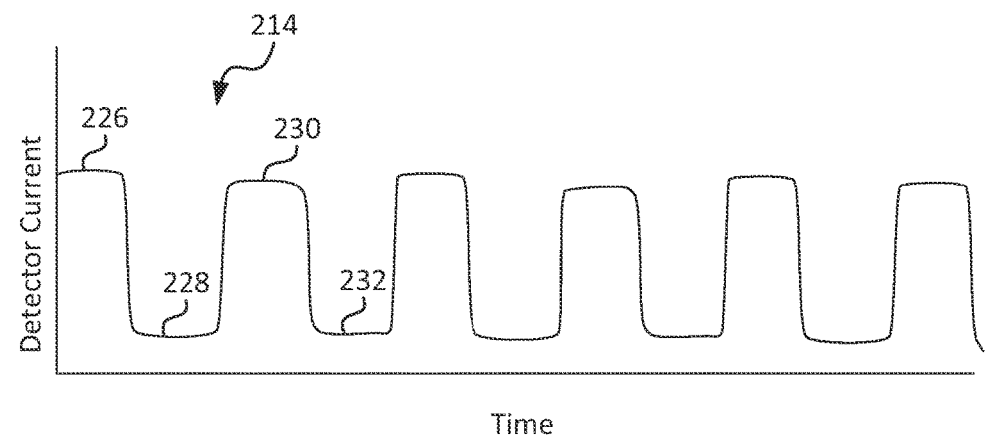
FIG. 2B shows an illustrative plot of a detector signal that may be generated by a sensor in accordance with some embodiments of the present disclosure.

FIG. 2B shows an illustrative plot of detector current waveform 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with drive pulses driving one or more emitters of a light source, such as light source 130 of FIG. 1. For example, detector current peak 226 may be generated in response to a light source being driven by red light drive pulse 202 of FIG. 2A, and peak 230 may be generated in response to a light source being driven by IR light drive pulse 204. Valley 228 of detector current waveform 214 may be synchronous with periods of time during which no light is being emitted by the light source, or the light source is returning to dark, such as "off" period 220. While no light is being emitted by a light source during the valleys, detector current waveform 214 may not fall all of the way to zero.

It will be understood that detector current waveform 214 may be an at least partially idealized representation of a detector signal, assuming perfect light signal generation, transmission, and detection. It will be understood that an actual detector current will include amplitude fluctuations, frequency deviations, droop, overshoot, undershoot, rise time deviations, fall time deviations, other deviations from the ideal, or any combination thereof. It will be understood that the system may shape the drive pulses shown in FIG. 2A in order to make the detector current as similar as possible to idealized detector current waveform 214.

Referring back to FIG. 1, front end processing circuitry 150, which may receive a detection signal, such as detector current waveform 214, may include analog conditioning 152, analog-to-digital converter (ADC) 154, demultiplexer 156, digital conditioning 158, decimator/interpolator 160, and ambient subtractor 162.

Analog conditioning 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof.

The conditioned analog signal may be processed by analog-to-digital converter 154, which may convert the conditioned analog signal into a digital signal. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a red component corresponding to peak 226, an IR component corresponding to peak 230, and at least one ambient component corresponding to valley 230. Demultiplexer 156 may operate on detector current waveform 214 of FIG. 2B to generate a red signal, an IR signal, a first ambient signal (e.g., corresponding to the ambient component corresponding to valley 230 that occurs immediately after the peak 226), and a second ambient signal (e.g., corresponding to the ambient component corresponding to valley 230 that occurs immediately after the IR component 230). Demultiplexer 156 may operate under the control of control circuitry 110. For example, demultiplexer 156 may use timing control signals from control circuitry 110 to identify and separate out the different components of the detector signal.

Digital conditioning 158 may perform any suitable digital conditioning of the detector signal. Digital conditioning 158 may include any type of digital filtering of the signal (e.g., low pass, high pass, band pass, notch, or any other suitable filtering), amplifying, performing an operation on the signal, performing any other suitable digital conditioning, or any combination thereof.

Decimator/interpolator 160 may decrease the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Ambient subtractor 162 may operate on the digital signal. In some embodiments, ambient subtractor 162 may remove dark or ambient contributions to the received signal.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signal, by analog conditioning 152 to map the expected range of the signal to the full or close to full output range of analog-to-digital converter 154. The output value of analog-to-digital converter 154, as a function of the total analog gain applied to the detection signal, may be given as:

ADC Value=Total Analog Gain×[Ambient Light+ LED Light]

Ideally, when ambient light is zero and when the light source is off, the analog-to-digital converter 154 will read just above the minimum input value. When the light source is on, the total analog signal provided to analog-to-digital converter 154 may be modified such that the output of analog-to-digital converter 154 is close to the full scale without saturating. Modifications of the signal may include subtracting an estimate signal, applying an offset, applying a gain, any other suitable modifications, or any combination thereof. These modifications may allow the full or a substantial amount of the dynamic range of analog-to-digital converter 154 to be used for representing the detection signal, thereby increasing the resolution of the converted signal. In some embodiments, where the input to the analog-to-digital to converter maps to a relatively smaller number of analog-to-digital conversion bits, the output of analog-to-digital converter 154 may include fewer bits of resolution. In some embodiments, the total analog gain and other modifications may be adjusted by such that small changes in the light level incident on the detector do not cause saturation of analog-to-digital converter 154. In some embodiments, passive or active filtering or signal modification techniques may be employed to reduce the contribution of a noise or other undesirable signal component from the input to analog-to-digital converter 154, thereby increasing the effective resolution of the digitized signal.

In some embodiments, light drive parameters may be configured to produce light pulses from multiple emitters (e.g., IR pulses and red pulses) that result in similar amplitude detected signals being received by the ADC. If the same current level were applied to red and IR light emitters, the amplitude of the detected signals received by the ADC may be different due to, for example, different levels of absorption and efficiencies of the light emitters. Therefore, the current level of the light drive signal for different light emitters may be set to different values such that the detected signal amplitudes are similar.

Back end processing circuitry 170 may include processor 172 and memory 174. Processor 172 may be adapted to execute software, which may include an operating system and one or more applications, as part of performing the functions described herein. Processor 172 may receive and further process sensor signals received from front end processing circuitry 150. For example, processor 172 may determine one or more physiological parameters based on the received physiological signals. Processor 172 may include an assembly of analog or digital electronic components. Processor 172 may calculate physiological information. For example, processor 172 may compute one or more of blood oxygen saturation (e.g., arterial, venous, or both), pulse rate, respiration rate, respiration effort, blood pressure, hemoglobin concentration (e.g., oxygenated, deoxygenated, and/or total), any other suitable physiological parameters, or any combination thereof. Processor 172 may perform any suitable signal processing of a signal, such as any suitable band-pass filtering, adaptive filtering, closed-loop filtering, any other suitable filtering, and/or any combination thereof. Processor 172 may also receive input signals from additional sources not shown. For example, processor 172 may receive an input signal containing information about treatments provided to the subject from user interface 180. Additional input signals may be used by processor 172 in any of the calculations or operations it performs in accordance with back end processing circuitry 170 or monitor 104.

Memory 174 may include any suitable computer-readable media capable of storing information that can be interpreted by processor 172. In some embodiments, memory 174 may store calculated values such as light drive parameter limits. Calculated values may be stored in a memory device for later retrieval. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with user interface 180 and communication interface 190.

User interface 180 may include user input 182, display 184, and speaker 186. User interface 180 may include, for example, any suitable device such as one or more medical devices (e.g., a medical monitor that displays various physiological parameters, a medical alarm, or any other suitable medical device that either displays physiological parameters or uses the output of back end processing 170 as an input), one or more display devices (e.g., monitor, personal digital assistant (PDA), mobile phone, tablet computer, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth.

In an embodiment, the subject may be a medical patient and display 184 may exhibit a list of values which may generally apply to the patient, such as, for example, age ranges or medication families, which the user may select using user input 182. Additionally, display 184 may display, for example, an estimate of a subject's blood oxygen saturation generated by monitor 104 (e.g., an "SpO$_2$" measurement), pulse rate information, respiration rate and/or effort information, blood pressure information, hemoglobin concentration information, any other parameters, and any combination thereof. Display 184 may include any type of display such as a cathode ray tube display, a flat panel display such as a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, communications buses, communications protocols, device identification protocols, any other suitable hardware or software, or any combination thereof. Communications interface 190 may be configured to allow wired communication (e.g., using USB, RS-232, Ethernet, or other standards), wireless communication (e.g., using WiFi, IR, WiMax, BLUETOOTH, USB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In other embodiments, the functionality of one or more of the components may be performed in a different order or may not be required. In an embodiment, all of the components of physiological monitoring system 100 can be realized in processor circuitry.

Figure 3:
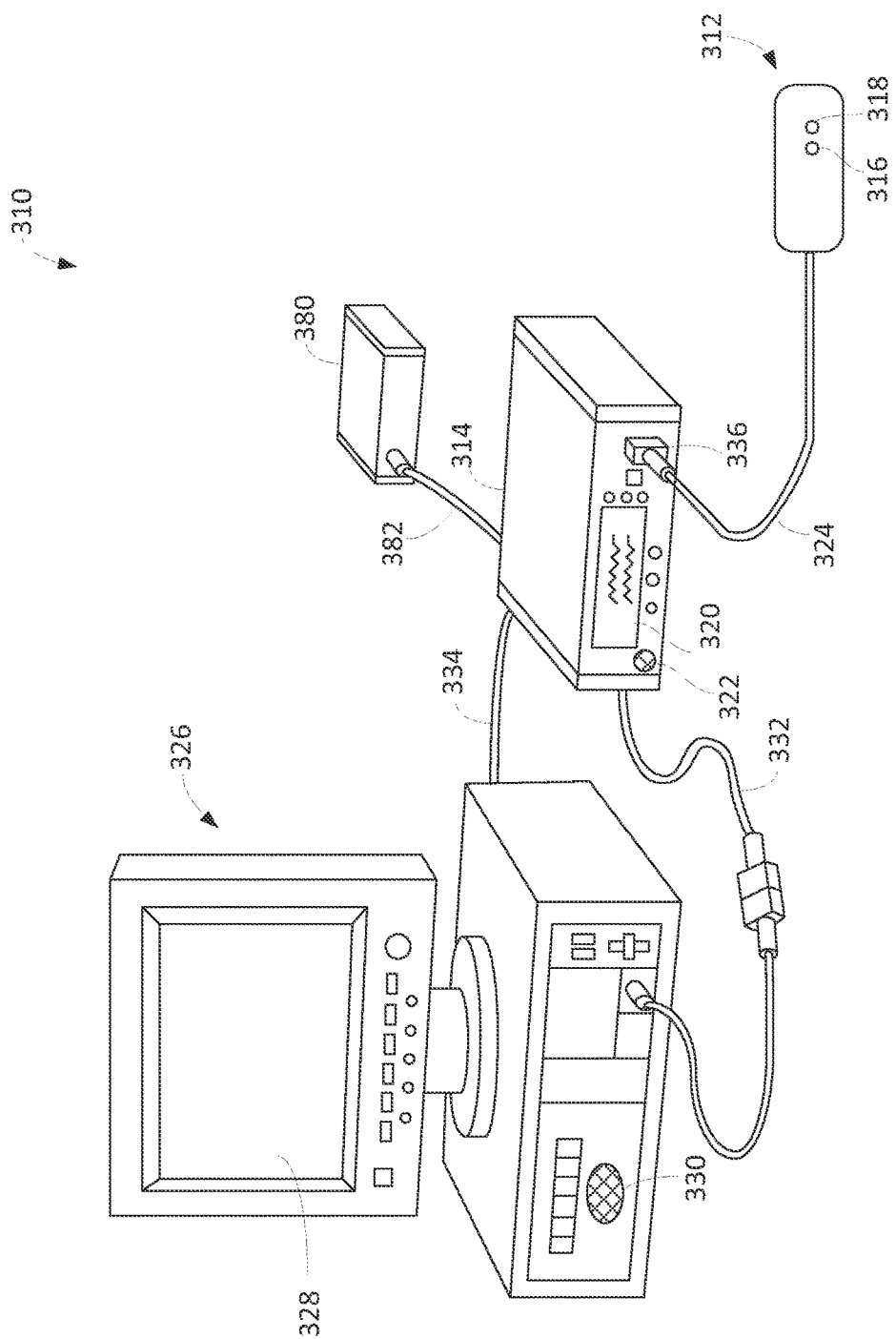
FIG. 3 is a perspective view of an illustrative physiological monitoring system in accordance with some embodiments of the present disclosure.

FIG. 3 is a perspective view of an illustrative physiological monitoring system 310 in accordance with some embodiments of the present disclosure. In some embodiments, one or more components of physiological monitoring system 310 may include one or more components of physiological monitoring system 100 of FIG. 1. Physiological monitoring system 310 may include sensor unit 312 and monitor 314. In some embodiments, sensor unit 312 may be part of an oximeter. Sensor unit 312 may include one or more light source 316 for emitting light at one or more wavelengths into a subject's tissue. One or more detector 318 may also be provided in sensor unit 312 for detecting the light that is reflected by or has traveled through the subject's tissue. Any suitable configuration of light source 316 and detector 318 may be used. In an embodiment, sensor unit 312 may include multiple light sources and detectors, which may be spaced apart. Physiological monitoring system 310 may also include one or more additional sensor units (not shown) that may, for example, take the form of any of the embodiments described herein with reference to sensor unit 312. An additional sensor unit may be the same type of sensor unit as sensor unit 312, or a different sensor unit type than sensor unit 312 (e.g., a photoacoustic sensor). Multiple sensor units may be capable of being positioned at two different locations on a subject's body.

In some embodiments, sensor unit 312 may be connected to monitor 314 as shown. Sensor unit 312 may be powered by an internal power source, e.g., a battery (not shown). Sensor unit 312 may draw power from monitor 314. In another embodiment, the sensor may be wirelessly connected (not shown) to monitor 314. Monitor 314 may be configured to calculate physiological parameters based at least in part on data relating to light emission and light detection received from one or more sensor units such as sensor unit 312. For example, monitor 314 may be configured to determine pulse rate, respiration rate, respiration effort, blood pressure, blood oxygen saturation (e.g., arterial, venous, or both), hemoglobin concentration (e.g., oxygenated, deoxygenated, and/or total), any other suitable physiological parameters, or any combination thereof. In some embodiments, calculations may be performed on the sensor units or an intermediate device and the result of the calculations may be passed to monitor 314. Further, monitor 314 may include display 320 configured to display the physiological parameters or other information about the system. In the embodiment shown, monitor 314 may also include a speaker 322 to provide an audible sound that may be used in various other embodiments, such as for example, sounding an audible alarm in the event that a subject's physiological parameters are not within a predefined normal range. In some embodiments, physiological monitoring system 310 may include a stand-alone monitor in communication with the monitor 314 via a cable or a wireless network link. In some embodiments, monitor 314 may be implemented as display 184 of FIG. 1.

In some embodiments, sensor unit 312 may be communicatively coupled to monitor 314 via a cable 324 at port 336. Cable 324 may include electronic conductors (e.g., wires for transmitting electronic signals from detector 318), optical fibers (e.g., multi-mode or single-mode fibers for transmitting emitted light from light source 316), any other suitable components, any suitable insulation or sheathing, or any combination thereof. In some embodiments, a wireless transmission device (not shown) or the like may be used instead of or in addition to cable 324. Monitor 314 may include a sensor interface configured to receive physiological signals from sensor unit 312, provide signals and power to sensor unit 312, or otherwise communicate with sensor unit 312. The sensor interface may include any suitable hardware, software, or both, which may be allow communication between monitor 314 and sensor unit 312.

In some embodiments, physiological monitoring system 310 may include calibration device 380. Calibration device 380, which may be powered by monitor 314, a battery, or by a conventional power source such as a wall outlet, may include any suitable calibration device. Calibration device 380 may be communicatively coupled to monitor 314 via communicative coupling 382, and/or may communicate wirelessly (not shown). In some embodiments, calibration device 380 is completely integrated within monitor 314. In some embodiments, calibration device 380 may include a manual input device (not shown) used by an operator to manually input reference signal measurements obtained from some other source (e.g., an external invasive or non-invasive physiological measurement system).

In the illustrated embodiment, physiological monitoring system 310 includes a multi-parameter physiological monitor 326. The monitor 326 may include a cathode ray tube display, a flat panel display (as shown) such as a liquid crystal display (LCD) or a plasma display, or may include any other type of monitor now known or later developed. Multi-parameter physiological monitor 326 may be configured to calculate physiological parameters and to provide a display 328 for information from monitor 314 and from other medical monitoring devices or systems (not shown). For example, multi-parameter physiological monitor 326 may be configured to display an estimate of a subject's blood oxygen saturation and hemoglobin concentration generated by monitor 314. Multi-parameter physiological monitor 326 may include a speaker 330.

Monitor 314 may be communicatively coupled to multi-parameter physiological monitor 326 via a cable 332 or 334 that is coupled to a sensor input port or a digital communications port, respectively and/or may communicate wirelessly (not shown). In addition, monitor 314 and/or multi-parameter physiological monitor 326 may be coupled to a network to enable the sharing of information with servers or other workstations (not shown). Monitor 314 may be powered by a battery (not shown) or by a conventional power source such as a wall outlet.

In some embodiments, any of the processing components and/or circuits, or portions thereof, of FIGS. 1 and 3, including sensors 102 and 312 and monitors 104, 314, and 326, may be referred to collectively as processing equipment. For example, processing equipment may be configured to amplify, filter, sample and digitize an input signal from sensor 102 or 312 (e.g., using an analog-to-digital converter), and calculate physiological information from the digitized signal. Processing equipment may be configured to generate light drive signals, amplify, filter, sample and digitize detector signals, sample and digitize other analog signals, calculate physiological information from the digitized signal, perform any other suitable processing, or any combination thereof. In some embodiments, all or some of the components of the processing equipment may be referred to as a processing module.

Figure 4:
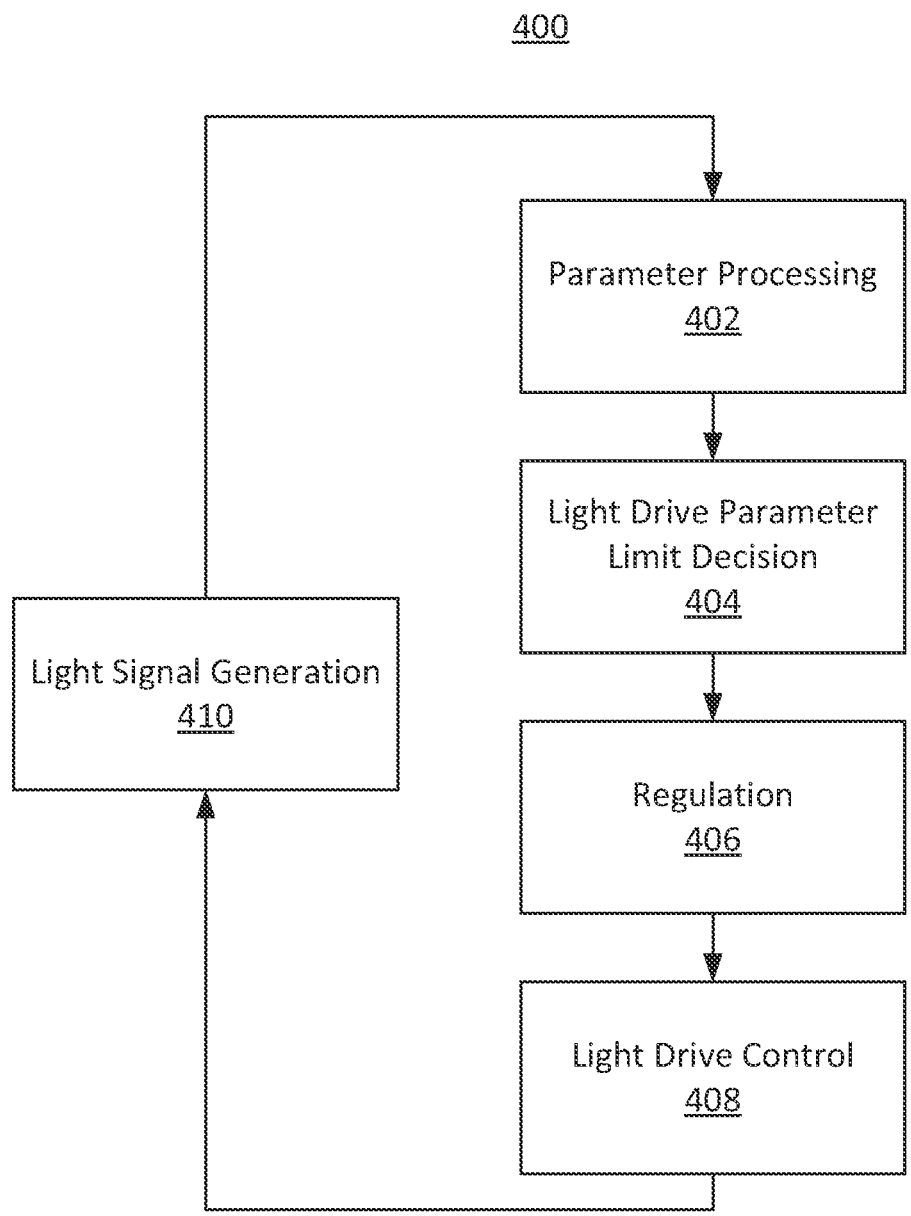
FIG. 4 shows a block diagram of an illustrative system for light signal generation in accordance with some embodiments of the present disclosure.

FIG. 4 shows a block diagram of illustrative system 400 for light signal generation in accordance with some embodiments of the present disclosure. System 400 includes parameter processing module 402, light drive parameter limit decision module 404, regulation module 406, light drive control module 408, and light signal generation module 410.

Parameter processing module 402 may include, for example, one or more elements of front end processing 150 of FIG. 1, back end processing 170 of FIG. 1, any other suitable elements, or any combination thereof. Parameter processing may receive one or more input signals. Input signals may include received light signals, such as those detected by detector 140 of FIG. 1. For example, a photodetector may generate an electrical current that corresponds to an amount of detected light. In some embodiments, more than one signal may be received, where each signal corresponds to a particular wavelength of light. For example, parameter processing 402 may receive a red signal and an IR signal. In some embodiments, multiplexed signals (e.g., time division multiplexed, frequency division multiplexed, phase division multiplexed, any other suitable multiplexing, or any combination thereof) may be demultiplexed. Demultiplexing may take place before parameter processing module 402, in parameter processing module 402, at any other suitable point, or any combination thereof. Input signals provided to parameter processing module 402 may additionally or alternatively include other physiological sensor signals such as ECG signals, respiration monitor signals, patient motion signals, pressure monitor signals, any other suitable signals, or any combination thereof. In some embodiments, parameter processing module 402 may additionally or alternatively receive physiological parameters (e.g., from other modules or physiological monitors) as an input.

Parameter processing module 402 may output processed signal parameters, processed physiological parameters, processed system parameters, received physiological parameters, any other suitable parameters, or any combination thereof. Signal parameters may include, for example, percent modulation, nAv, signal amplitude, signal-to-noise ratio, signal quality, any other suitable signal parameters, or any combination thereof. Physiological parameters may include physiological parameters determined based on received signals. For example, physiological parameters may include $SpO_2$, pulse rate, respiration rate, respiration effort, blood pressure, hemoglobin concentration (e.g., oxygenated, deoxygenated, and/or total), cardiac output, patient motion, any other suitable parameters, or any combination thereof. In some embodiments, additional signals may be determined from the determined parameters, for example the standard deviation or variance of the $SpO_2$ values. System parameters may include, for example, a probe-off condition parameter, the type of probe or probes attached to the system, battery charge levels, power supply information, alarms, user input, any other suitable system parameters, or any combination thereof.

It will be understood that in some embodiments, physiological parameters may be determined in parameter processing module 402 based on received light signals, while in some embodiments, determined physiological parameters may be received by parameter processing module 402 from other processing modules or physiological monitors.

Light drive parameter limit decision module 404 may include, for example, one or more elements of back end processing 170 of FIG. 1. Light drive parameter limit decision module 404 may receive information from parameter processing module 402. The information may include, for example, one or more parameters of the received sensor signals. In an example, parameter processing module 402 may receive a red light signal, determine an nAv or percent modulation parameter of that signal, and pass that parameter to light drive parameter limit decision module 404.

Light drive parameter limit decision module 404 may make decisions based on information received from parameter processing module 402. In some embodiments, decisions may be made to determine whether one or more parameters are within a particular range or band of values, or above or below a threshold. For example, the system may decide if a pulse rate is in a low, acceptable, or high range, or if the pulse rate is above or below a threshold. In another example, the system may decide if a percent modulation is in an acceptable range. In another example, the system may decide if a sensor state indication, such as an indication of whether a probe is properly connected to a subject, is indicative of a valid signal being received.

Decisions made by light drive parameter limit decision module 404 may include hysteresis and other time-dependent processing that adjusts the limits between states based on the history or trajectory of the parameter. For example, in determining if a pulse rate is in an acceptable range, an excursion from the presently occupied range of more than a particular amount of time may be required for the extant decision to be updated. In another example, an $SpO_2$ value may be considered acceptable if above 94%, but upon recovering from a low $SpO_2$ event (e.g., where the value has decreased to 85%), the $SpO_2$ value may be considered in a low $SpO_2$ range until it exceeds 96%. It will be understood that hysteresis may include time-dependent limits, value-dependent limits, any other suitable hysteresis, or any combination thereof. It will also be understood that hysteresis need not be symmetrical. For example, the excursion required to decrease a setting may be larger than the excursion to increase a setting. It will also be understood that hysteresis may be adjusted using any suitable technique and based on any suitable information. For example, the system may increase hysteresis limits in order to decrease switching when the switching rate is high, or may decrease hysteresis limits in order to allow more rapid switching.

In some embodiments, light drive parameter limit decision module 404 may generate one or more decisions that correspond to one or more parameters received from parameter processing module 402. In some embodiments, multiple decisions may be combined to generate a combined decision. The combined decision may be generated using a logical combination such as a logical AND. A logical AND combination may generate a "1" output when all of the inputs are "1," and may generate a "0" output when less than all of the inputs are "1." In an example, the system may generate a "1" decision for each individual parameter that is considered to be acceptable. The combined decision may be a "1" decision when all of the individual parameters are considered acceptable, and otherwise may be a "0" decision. It will be understood that the use of the AND combination is merely exemplary and that any suitable combination may be used. For example, decisions may be combined using algorithms, neural nets, weighted combinations, more complex logic, any other suitable combination, or any combination thereof. Further, the individual parameter decisions and the combination decision need not be binary decisions, but may also include continuous values, discrete values with more than two possible states, any other suitable values, or any combination thereof. The individual and combined decisions also need not be scalar quantities, and may include time information, trend information, any other suitable information, or any combination thereof.

Regulation module 406 may include, for example, one or more elements of back end processing 170 of FIG. 1. Regulation module 406 may receive information from light drive parameter limit decision module 404. The received information may include individual parameter decisions and/or combined decisions. For example, regulation module 406 may receive a combined decision that indicates whether or not all of the individual parameters are in respective desired ranges.

Regulation module 406 may regulate the setting of the light drive parameter limit. For example, regulation module 406 may include a state machine with a first state and a second state corresponding to two different values of the light drive parameter limit. For example, where the light drive parameter is a current, a first state may correspond to a first maximum current limit, and a second state may correspond to a second lower maximum current limit. The state machine may change state only when the combined decision is of a particular value. Thus, some decisions from light drive parameter limit decision module 404 may not result in a change, or an immediate change, in the light drive parameter limit. In some embodiments, a combined decision provided to regulation module 406 may need to be of a particular value and/or maintained for a particular amount of time in order for the state machine of regulation module 404 to change. For example, the state machine may be in a first state, and may change to the second state only if the combined decision is a "0" output and is maintained for a minimum duration, such as 20 seconds. The state machine may toggle back to the first state only if the combined decision is a "1" output and is maintained for a same or different minimum duration, such as at least 30 seconds. It will be understood that these times and values are merely exemplary. It will also be understood that the use of a state machine is merely exemplary and that any suitable technique for regulation may be used. For example, where the combined decision is a continuously variable output represented as a weighted combination, regulation module 406 may include an algorithm to modulate the impact of those changes on the limit. It will also be understood that in some embodiments, regulation module 406 may be omitted and that the variability of the light drive parameter need not be regulated.

Light drive control module 408 may include, for example, one or more elements of control circuitry 110 of FIG. 1 and/or light drive circuitry 120 of FIG. 1. Light drive control module 408 may receive information from regulation module 406. The received information may include a light drive parameter limit, which may be determined based on the state selected by the state machine from the regulation module 406. In some embodiments, light drive control module 408 may compare the light drive parameter limit with the extant light drive parameter. For example, light drive control module 408 may check if the extant parameter exceeds the limit. When the parameter exceeds the limit, light drive control 408 may update the light drive parameter to be a value less than or equal to the limit. When the parameter does not exceed the limit, light drive control 408 need not change the parameter. In an example, where the light drive parameter is the light drive current I and the light drive parameter limit is a maximum current $I_{max}$, light drive control module 408 may set I to a value less than or equal to $I_{max}$ when I is greater than $I_{max}$, and may leave I unchanged when I is less than $I_{max}$. For example, I may be set to one-half of its previous value when I exceeds $I_{max}$. It will be understood that the aforementioned steps are merely exemplary and that the system may determine a light drive parameter based on the decisions using any suitable technique. For example, the output of regulation may be used to set a light drive current directly, rather than comparing a parameter limit to a parameter. In another example, the system may adjust the light drive parameter based on the limit, regardless of whether the limit is exceeded. In another example, the current may be reduced by a predetermined absolute or relative amount when it exceeds a limit, rather than being set to equal the limit. It will also be understood that the use of a light drive current parameter in this technique is merely exemplary and that this technique may be used to control any suitable parameter such as light drive pulse shaping, duty cycle, selection of a light drive algorithm, selection of light emitters, gain level, brightness, any other suitable parameters, or any combination thereof. In some embodiments, the extant light drive parameter is not compared with the light drive parameter limit. For example, light drive control module 408 may use the light drive parameter limit to determine a new light drive parameter regardless of the extant light drive parameter. The new light drive parameter may be the same as or different than the extant light drive parameter.

Light signal generation module 410 may include, for example, elements of light drive circuitry 120 of FIG. 1 and/or sensor 102 of FIG. 1. For example, light signal generation module 410 may receive a signal from light drive control module 408 and may generate a photonic light signal based on that received light signal. In an example, light signal generation module 410 may include one or more light emitting diodes of one or more wavelength. The signal received from light drive control 408 may include a current that is supplied to the light emitting diodes, in order to generate a photonic light signal. In some embodiments, information received from the light drive control signal may include a control signal that is used to generate an electrical light drive signal in light signal generation module 410. Light emitters may include light emitting diodes, light emitting diode lasers, any other suitable light source, or any combination thereof.

In some embodiments, some of the light emitted by light signal generation module 410 may be provided to a subject. The light may be partially attenuated by interactions with the subject and the system may detect light that is reflected and/or transmitted by the subject. The system may provide the detected light signal to parameter processing module 402.

Figure 5:
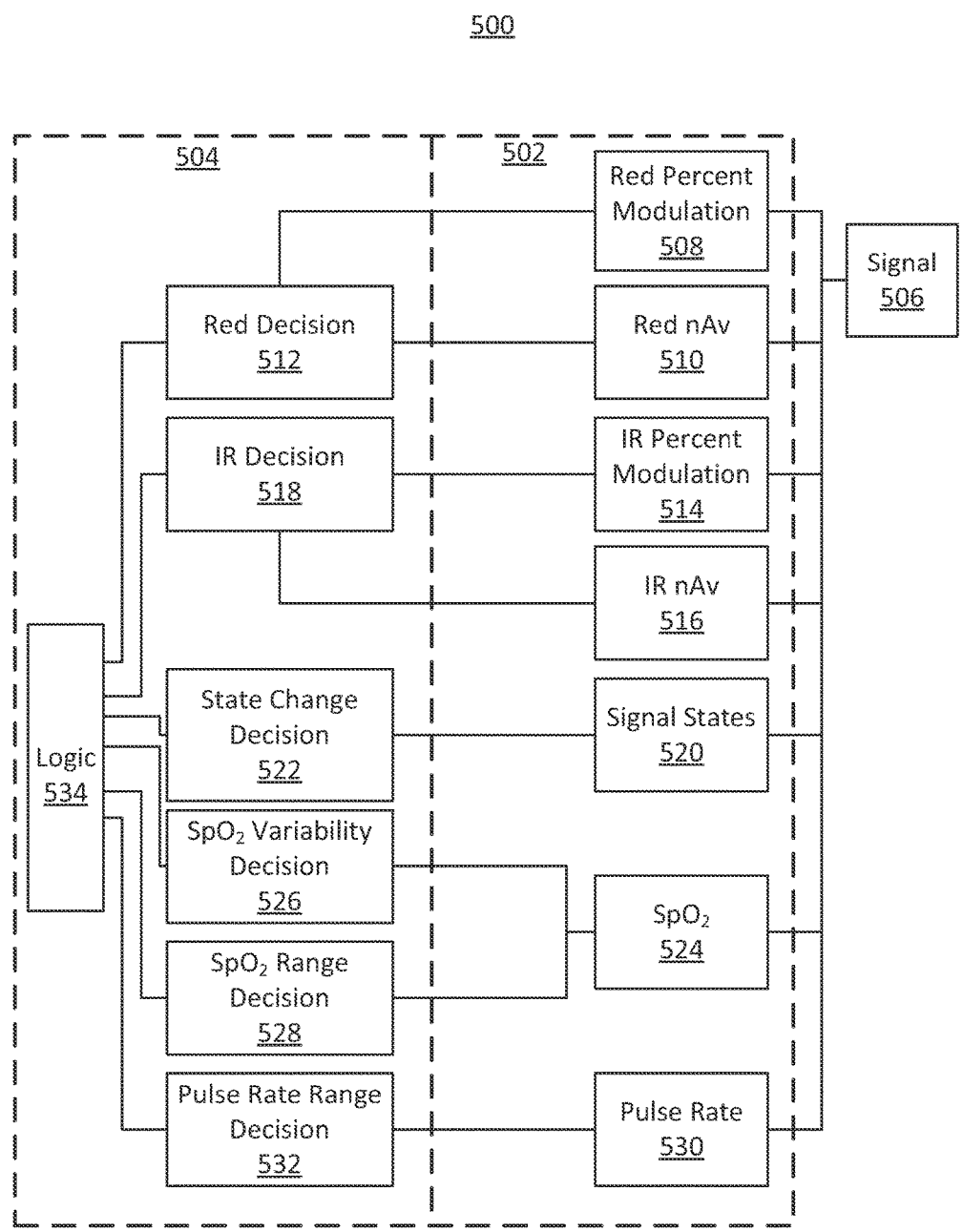
FIG. 5 shows a block diagram of an illustrative system including parameter processing and a drive parameter limit decision in accordance with some embodiments of the present disclosure.

FIG. 5 shows a block diagram of illustrative system 500 including parameter processing module 502 and light drive parameter limit decision module 504 in accordance with some embodiments of the present disclosure. In some embodiments, parameter processing module 502 corresponds to parameter processing module 402 of FIG. 4. In some embodiments, light drive parameter limit decision module 504 corresponds to light drive parameter limit decision module 404 of FIG. 4.

Signal 506 is provided to one or more elements of parameter processing module 502. Signal 506 may include any suitable signal or signals. For example, signal 506 may include a detected light signal, one or more demultiplexed signals derived from a detected light signal, a signal including physiological parameters, a signal from a physiological sensor, a signal from a physiological monitor, any other suitable signal, or any combination thereof.

Parameter processing module 502 may determine one or more parameters based at least in part on signal 506. Where the signal includes red and IR wavelength signal components, parameters may include red percent modulation 502, red nAv 510, IR percent modulation 514, and IR nAv 516. It will be understood that the use of red and IR wavelengths is merely exemplary and that any suitable number of any suitable wavelength light signals may be used.

Signal states 520 may determine states of signal 506, states of a physiological monitor, states of a probe or sensor, any other suitable information, or any combination thereof. For example, states may include a probe-off condition. Probe-off conditions may correspond to the situation where a probe has disconnected from a subject, moved out of position on a subject, become disconnected from a monitor, become displaced in any other suitable manner, or any combination thereof. Probe-off conditions may be detected, for example, based on the presence of a signal, based on comparisons between signals, based on signal behavior, based on ambient signal levels, based on a probe-off indicator signal, based on any other suitable information, or any combination thereof.

$SpO_2$ 524 may include blood oxygen saturation information. The oxygen saturation may be determined in parameter processing module 502 based on received light signals, may be determined external to parameter processing module 502 and provided to $SpO_2$ 524, may be determined using any other suitable technique, or any combination thereof. The information of $SpO_2$ 524 may include any suitable hemodynamic information, for example, oxygen saturation, carbon dioxide saturation, total hemoglobin, any other suitable information, or any combination thereof. Pulse rate 530 may include any suitable cardiac rhythm information. For example, cardiac rhythm information may include pulse rate (e.g., in beats-per-minute), an interval between cardiac pulses, the length of cardiac pulses, intervals between particular features of a light signal, intervals between particular features of an electrical signal, any other suitable information, or any combination thereof.

It will be understood that parameter processing module 502 may include other parameters not shown in FIG. 5. The other parameters may be determined by processing module 502 or received by processing module 502 from other modules or systems. For example, parameter processing may include physiological parameters such as cardiac output, blood pressure, any other suitable physiological parameter, or any combination thereof. Parameter processing may include subject information such as medical history, treatment information, age, weight, height, gender, medication, illness, any other suitable subject information, or any combination thereof. Parameter processing may also include user input and predetermined information.

Parameter processing module 502 may include suitable processing of the determined parameters. Processing may include filtering such as outlier rejection, averaging, weighted averaging, time-dependent filtering (e.g., infinite impulse response filtering, finite impulse response filtering), adaptive filtering, any other suitable filtering, or any combination thereof. In an example, outlier rejection and weighted averaging may be applied separately to the outputs of red percent modulation 508, red nAv 510, IR percent modulation 514, and IR nAv 516. For example, weights may be applied such that decisions corresponding to red light are weighted higher than decisions corresponding to IR light. Filtering and other processing may also combine multiple parameters. For example, filter parameters applied to the red and IR parameters may be dependent upon the $SpO_2$ value.

Light drive parameter limit decision module 504 may make decisions based on the parameters of parameter processing module 502. Decisions may include, for example, whether a particular parameter is within a desired range. Decisions may include hysteresis. For example, a decision may only change if a particular parameter exceeds a limit by a particular amount and/or a particular amount of time. Desired ranges may be predetermined, based on user input, based on information regarding the subject such as medical history, based on any other suitable information, or any combination thereof. The outputs of the decision modules may include a binary vote such as "0" or "1." That is, the output may be "1" when a parameter is in an acceptable range, or when the output has been recently changed to "1," and the output may be "0" when the output is not in an acceptable range, or when the output has been recently changed to "0." In some embodiments outputs may include continuous outputs, discrete outputs with more than two values, any other suitable outputs, or any combination thereof.

In some embodiments, red decision module 512 may make decisions based on information from red percent modulation 508 and red nAv 510. IR decision module 518 may make decisions based on information from IR percent modulation 514 and IR nAv 516. State change decision module 522 may make decisions based on the information provided by signal states 520. $SpO_2$ variability decision module 526 may make decisions based on the variability of the $SpO_2$. Variability may include, for example, the standard deviation of the signal over a particular time window. $SpO_2$ range decision module 528 may make decisions based on the level of the $SpO_2$. It will be understood that the decisions made by $SpO_2$ variability decision module 526 and range decision module 528 may be similarly decided about other physiological parameters not shown. Pulse rate range decision module 532 may make decisions about the level of the pulse rate and other information received from hear rate 530.

Logic 534 may receive information regarding the decisions made by the decision modules of light drive parameter limit decision module 504. Logic 534 may combine the decisions to generate a combined decision using any suitable technique. In an example, logic 534 may use a logical AND operation to combine binary outputs from the decision modules. Logic 534 may use algorithms, neural nets, weighted combinations, more complex logic, any other suitable combination, or any combination thereof. The output of logic 534 need not be a binary decision, but may also be a continuous value, a discrete value with more than two possible states, any other suitable value, or any combination thereof. The inputs and outputs of logic 534 need not be scalar quantities, and may include time information, trend information, any other suitable information, or any combination thereof.

It will be understood that the parameters of parameter processing module 502 are merely exemplary and that any suitable parameters may be used. In some embodiments, respiration parameters may be included in parameter processing module 502. Respiration parameters may include, for example, respiration rate timing, respiration rate, respiration rate age, an arrhythmia flag, central apnea detection, any other suitable parameters, or any combination thereof. In some embodiments, respiration parameters may be determined based on signal 506. For example, signal 506 may include a light signal from a pulse oximeter, and the system may determine an $SpO_2$ parameter, nAv and percent modulation signals parameters, and a respiration rate parameter based on signal 506.

Light drive parameter limit decision module 504 may make decisions based on the respiration parameters. For example, decisions may be made based on whether the parameters are in an acceptable range. Acceptable ranges may include, for example, a respiration rate between 10 and 25 breaths per minute, a respiration rate age of less than 45 seconds, an arrhythmia flag set to false, and a central apnea flag set to false.

In some embodiments, the parameters of parameter processing module 502 may be selected based in part on the physiological parameters determined by the system. For example, the system may use respiration parameters in parameter processing module 502 to determine an amount of available power when the system determines respiration information. In another example, the system may use both respiration parameters and SpO$_2$ parameters when it determines both respiration and SpO$_2$ information about a subject. It will be understood that the system may use any suitable combination of oxygen saturation parameters, respiration parameters, or any other suitable parameters to determine a decision in light drive parameter limit decision module 504.

Figure 6:
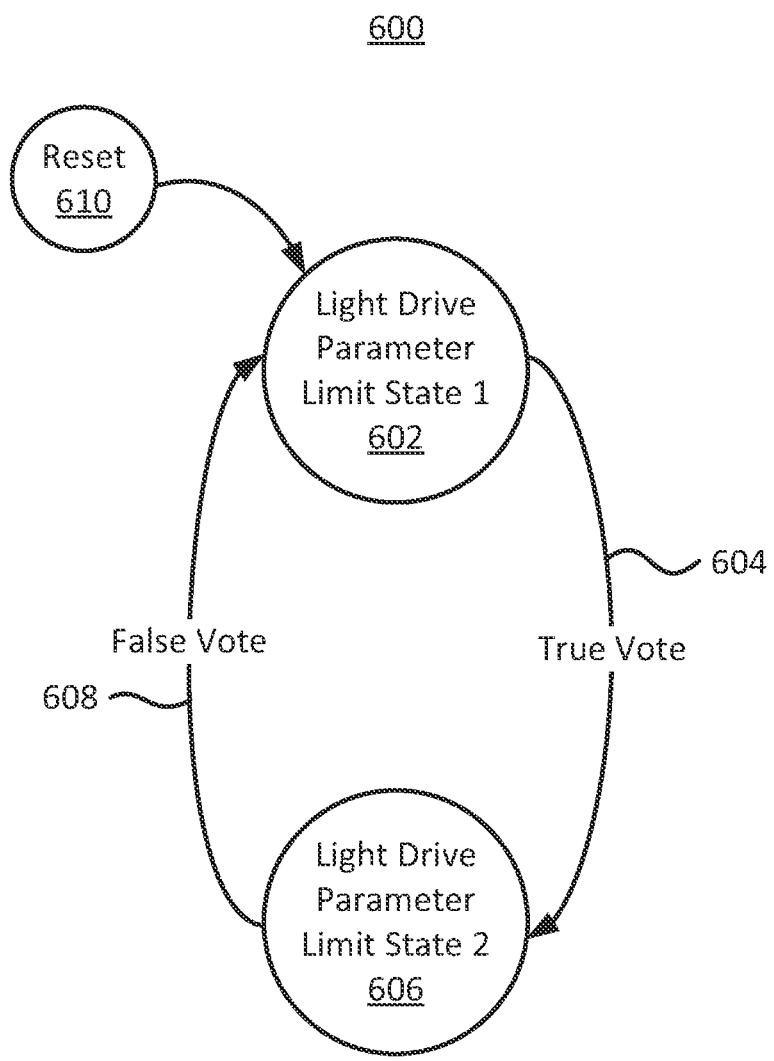
FIG. 6 shows a block diagram of a regulation module in accordance with some embodiments of the present disclosure.

FIG. 6 shows a block diagram of regulation module 600 in a pulse oximeter in accordance with some embodiments of the present disclosure. In some embodiments, regulation module 600 may correspond to regulation module 406 of FIG. 4. Regulation module 600 includes a state machine that is operated based on input to regulation module. Input may include the output of logic 534 of FIG. 5, the output of light drive parameter limit decision module 404 of FIG. 4, user input, any other suitable input, or any combination thereof. Regulation module 600 may include two states. Light drive parameter limit state 1 602 may be a first state and light drive parameter limit state 2 606 may be a second state. In some embodiments, the light drive parameter limit may be a first or second value depending on the state in which the state machine exists. In an example where the light drive parameter limit is I$_{max}$, the limit may be 50 mA in state 1 602 and 25 mA in state 2 604.

In the illustrated example, the state machine may only be in one of the two states. It will be understood that regulation module 600 may include any suitable number of states that correspond to any suitable number of parameter limits. For example, the state machine may include three states, and the limit may be of one of three values, each corresponding to a state. It will also be understood that regulation module 600 need not use a state machine, and that the limit may be determined using any suitable technique such as an algorithm, neural net, other processing technique, or any combination thereof.

In some embodiments, regulation module 600 may initially be in state 1 602.

Regulation module 600 may enter state 1 602 on initialization of the system or on receiving a reset, as indicated by reset input 610. Regulation module 606 may remain in state 1 602 until a true vote 604 is received, at which point regulation module may enter state 2 606. Regulation module 606 may remain in state 2 606 until a false vote 608 is received, at which point regulation module 600 may enter state 1. True vote 604 and false vote 608 may include any suitable qualifying parameters. For example, true vote 604 may include receiving an output of "1" from logic 534 for 10 seconds. In another example, receiving false vote 608 may include receiving an output of "0" from logic 534 for 15 seconds. It will be understood that receiving a vote may include receiving any suitable number of any suitable parameters, such as time information, trend information, logic output, other suitable inputs, or any combination thereof.

The following FIGS. 7-10 show illustrative plots used by the light drive parameter limit decision module to determine if a particular parameter is in a desired range. The plots include regions of hysteresis. As described above, any suitable hysteresis may be applied in the decision making, for example, differing cut-offs depending on trend, time-dependent hysteresis, any other suitable hysteresis, or any combination thereof. In some embodiments, hysteresis may be omitted. It will be understood that the specific ranges shown here are merely exemplary. In some embodiments, a value in a "Yes" region may correspond to an input of "1" to logic 534 of FIG. 5, while a value in the "No" region may correspond to an input of "0" to logic 534 of FIG. 5. The output to logic 534 of FIG. 5 while in a hysteresis region may depend on the prior output; thus, when the value moves from the "Yes" region into the hysteresis region, the output may remain "Yes" until the value moves into the "No" region, or until the value remains in the hysteresis region for a minimum duration of time. It will also be understood that while the illustrative plots show "Yes" and "No" regions, that the system may use any suitable technique having any suitable number of regions. Further, regions may be assigned particular values. In another example, a continuous decision value may be assigned based on the input. In another example, hysteresis may be omitted from the plots.

Figure 7:
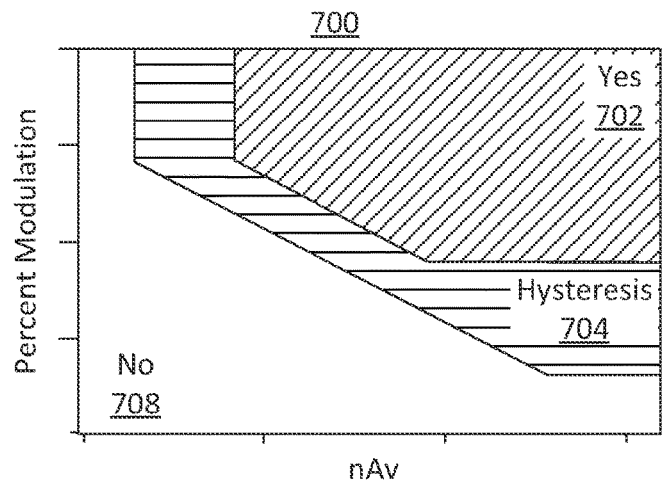
FIG. 7 shows an illustrative plot of decision step parameters related to nAv and percent modulation in accordance with some embodiments of the present disclosure.

FIG. 7 shows illustrative plot 700 of decision step parameters related to nAv and percent modulation in accordance with some embodiments of the present disclosure. Plot 700 shows a two-dimensional region, where the x-axis is defined in nAv and the y-axis is defined in percent modulation. Plot 700 may be used, for example, by red decision module 512 of FIG. 5 to make a determination based on inputs from red percent modulation 508 of FIG. 5 and red nAv 510 of FIG. 5. Yes region 702 indicates a region where the nAv and percent modulation are in an acceptable range. No region 708 indicates a region where the nAv and percent modulation are not in an acceptable range. Hysteresis region 704 indicates a region of hysteresis.

In an example of the hysteresis illustrated in plot 700, a signal with high percent modulation and high nAv may fall in Yes region 702, resulting in the output of a "1" logic result. If the percent modulation and nAv should change such that they correspond to a point in hysteresis region 704, the output would remain a logic "1" result. If the percent modulation and nAv change to indicate a point in No region 708, the output would change to a "0" result. Further, if the percent modulation and nAv should change to a point in hysteresis region 704 after leaving No region 708, the output would remain a "0" result. Thus in this example, when the value is in Hysteresis region 704, the output may remain the most recent "0" or "1" output. It will be understood that this implementation of hysteresis is merely exemplary and that changing from a "0" to "1" state may include time-dependent parameters, value-dependent parameters, additional inputs, any other suitable information, or any combination thereof. This hysteresis region 704 prevents rapid switching between states, for example when the value is hovering near the intersection between regions 708 and 704, or between regions 704 and 702.

Figure 8:
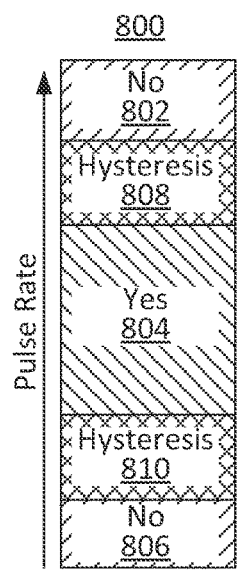
FIG. 8 shows an illustrative plot of a decision step parameter related to pulse rate in accordance with some embodiments of the present disclosure.

FIG. 8 shows illustrative plot 800 of a decision step parameter related to pulse rate in accordance with some embodiments of the present disclosure. Plot 800 shows a one-dimensional plot, where the y-axis is defined by pulse rate. Plot 800 may be used, for example, by pulse rate range decision module 532 of FIG. 5 to make a determination based on inputs from pulse rate 530 of FIG. 5. Yes region 804 indicates a range of pulse rates that are acceptable. No region 802 indicates a high pulse rate range. No region 806 indicates a low pulse rate range. Hysteresis ranges 808 and 810 indicate regions of hysteresis. In some embodiments, the acceptable range for pulse rate may be between 40 and 170 BPM and the hysteresis regions may be 2.5 BPM wide. This, however, is merely illustrative and the acceptable range for pulse rate and the size of the hysteresis regions may be any suitable range and size.

Figure 9:
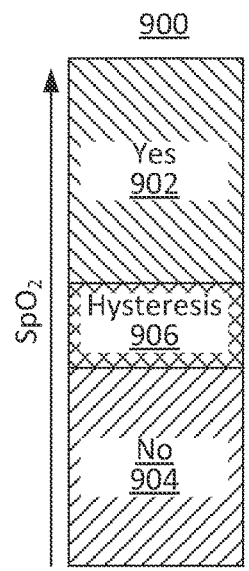
FIG. 9 shows an illustrative plot of a decision step parameter related to $SpO_2$ in accordance with some embodiments of the present disclosure.

FIG. 9 shows illustrative plot 900 of a decision step parameter related to $SpO_2$ in accordance with some embodiments of the present disclosure. Plot 900 shows a one-dimensional plot, where the y-axis is defined the $SpO_2$. Plot 900 may be used, for example, by $SpO_2$ range decision module 528 of FIG. 5 to make a determination based on inputs from $SpO_2$ 524 of FIG. 5. Yes region 902 indicates a range of $SpO_2$ that is acceptable. No region 904 indicates a low $SpO_2$ range. Hysteresis range 906 indicates a region of hysteresis. In some embodiments, hysteresis range 906 may span between 80% and 82.5% of $SpO_2$. This, however, is merely illustrative and the hysteresis range may be any suitable range.

Figure 10:
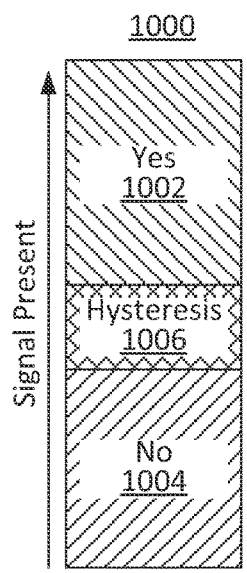
FIG. 10 shows an illustrative plot of a decision step parameters related to signal presence in accordance with some embodiments of the present disclosure.

FIG. 10 shows illustrative plot 1000 of a decision step parameter related to signal presence in accordance with some embodiments of the present disclosure. Plot 1000 shows a 1 dimensional plot, where the y-axis is defined by the presence of a signal, for example, a signal to noise ratio where higher values correspond to more signal and less noise. Plot 1000 may be used, for example, by state change decision module 522 of FIG. 5 to make a determination based on inputs from signal states 520 of FIG. 5. Yes region 1002 indicates a range of signal presence that is acceptable. No region 1004 indicates a low signal presence range. Hysteresis range 1006 indicates a region of hysteresis.

Figure 11:
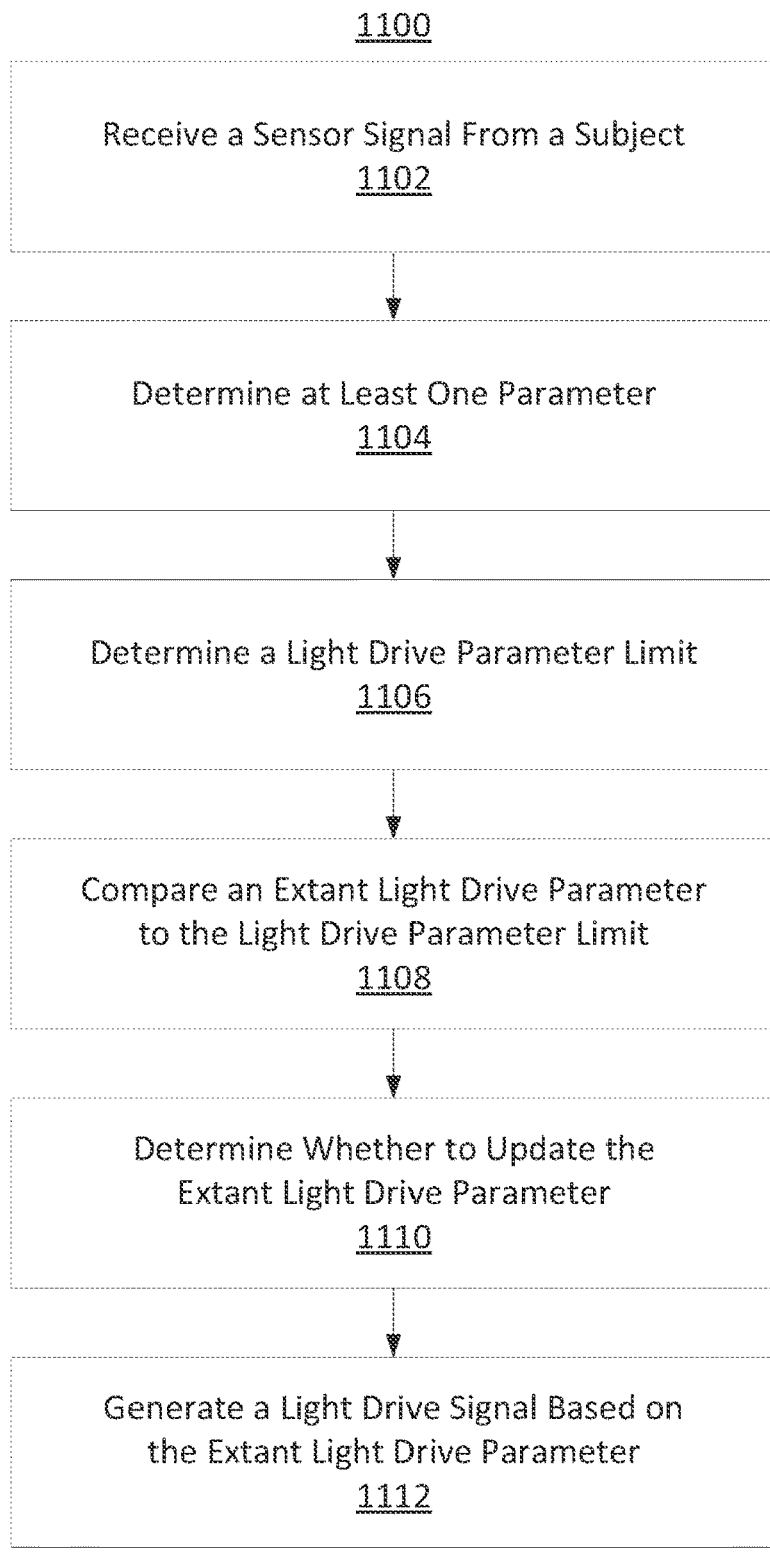
FIG. 11 shows an illustrative flow diagram including steps for generating a light drive signal in accordance with some embodiments of the present disclosure.

FIG. 11 shows illustrative flow diagram 1100 including steps for generating a light drive signal in accordance with some embodiments of the present disclosure. In some embodiments, steps of flow diagram 1100 include steps carried out by the modules illustrated in FIGS. 4-6.

Step 1102 includes receiving a sensor signal from a subject. A sensor signal may be received as described for parameter processing module 402 of FIG. 4. A sensor signal may include signal 506 of FIG. 5. In some embodiments, a sensor signal may be received from sensor 102 of FIG. 1. Receiving a sensor signal may include receiving an electrical and/or optical signal from a sensor. Sensors may include photodetectors that are included in a photoplethysmographic system. Sensors may additionally or alternatively include other photodetectors, ECG sensors, pulse rate sensors, blood analysis sensors, catheters, blood pressure sensors, any other suitable sensor, or any combination thereof. Sensor information may be received continuously, at regular intervals, at any other suitable time, or any combination thereof.

Step 1104 includes determining at least one parameter. Parameters may be determined based on the sensor signal. In some embodiments, the parameters determined by parameter processing module 402 of FIG. 4 and/or parameter processing module 502 of FIG. 5 may be determined in step 1104. Parameters may additionally or alternatively be determined based on sensor signal information, user input, information from any other suitable source, or any combination thereof. Determining at least one parameter may include filtering a determining parameter, as described above with regard to parameter processing module 502 of FIG. 5. Parameters may include signal parameters, such as percent modulation of any suitable signal and nAv, of any suitable signal. Suitable signals may include signals corresponding to a wavelength of detected light. For example, a component of a received light signal may correspond to detected light of a particular wavelength. It will be understood that any suitable indicator of signal strength, amplitude, or quality may be determined, including nAv, absolute amplitude, relative amplitude, signal-to-noise ratio, any other suitable metric, or any combination thereof. It will also be understood that any suitable metric of signal variability may be determined, including percent modulation, standard deviation over a particular time window, variance over a particular time window, any other suitable metric, or any combination thereof.

Parameters may include physiological parameters such as $SpO_2$, pulse rate, blood pressure, cardiac output, any other suitable parameter, or any combination thereof. Physiological parameters may be determined based on the received signal, may be included in the received signal, may be received from another processor, may be received based on user input, may be determined in any other suitable way, or any combination thereof. Physiological parameters may also include medical history information and medical chart data such as a subject's age, sex, height, weight, medication history, treatment history, medical history, any other suitable information, or any combination thereof.

Parameters may include signals based on other parameters. For example, a standard deviation and/or variance of an $SpO_2$ level may be determined. In some embodiments, parameters based on existing parameters may be used as a feedback signal.

Parameters may include system parameters such as signal states. Signal states may indicate, for example, a probe-off condition, the type of probe or probes attached to the system, battery charge levels, power supply information, alarms, user input, any other suitable system parameters, or any combination thereof.

Step 1106 includes determining a light drive parameter limit. In some embodiments, a light drive parameter limit may be determined in order to reduce power consumption. Determining a light drive parameter limit may include light drive parameter limit decision module 404 and regulation module 406 of FIG. 4. Determining a light drive parameter limit may include a decision made by light drive parameter limit decision module 504 of FIG. 5 and regulation module 600 of FIG. 6. In some embodiments, determining a light drive parameter limit includes making one or more decisions about the one more parameters determined or received in step 1104. Each of the one or more parameters may be included in making one or more decisions. In some embodiments, a decision may be made to determine if one or more parameters are in a desired band or range. For example, decisions may be made using the plots of FIGS. 7-10. The decisions may be combined to form a combined decision using any suitable technique, such as the techniques described for logic 534 of FIG. 5. The decisions and/or the combination logic may include any suitable hysteresis or other technique to limit overly rapid toggling of outputs. In some embodiments, more than one light drive parameter limit may be determined. For example, in a pulse oximeter with red and IR light emitters, a light drive parameter limit may be maintained for each wavelength emitter. In another example, a first light drive parameter limit corresponding to a maximum current and a second light drive parameter corresponding to maximum duty cycle may be determined in step 1106.

In some embodiments, decisions and/or a combined decision are provided to a regulation module. The regulation module may be used to determine a light drive parameter limit based on the decisions. In some embodiments, regulation may function as described for regulation module 600 of FIG. 6. In an example, where the light drive parameter is a light drive current, the determined light drive parameter limit may be either 25 mA or 50 mA, depending on the outcome of step 1106. It will be understood that these limits are merely exemplary and that any suitable number of any suitable values may be used as limits. It will also be understood that limits may be continuously varying. It will also be understood that limits need not be a light drive current, and may be any other suitable light drive parameter, such as light drive pulse shaping, duty cycle, selection of a light drive algorithm, selection of light emitters, gain level, brightness, any other suitable parameters, or any combination thereof.

Step 1108 includes comparing an extant light drive parameter to the light drive parameter limit. In some embodiments, step 1108 may be performed by light drive control module 408. In some embodiments, an extant light drive parameter is compared to the light drive parameter limit determined in step 1106. For example, where the light drive parameter is a light drive current I, the value of I may be compared to the $I_{max}$ determined in step 1106. In some embodiments, the comparison may determine if the value is greater than, less that, or equal to the limit. In some embodiments, the comparison may determine a relative or absolute difference.

Step 1110 includes determining whether to update the extant light drive parameter. In some embodiments, the system may determine whether to update the extant light drive parameter based on the comparison made in step 1108. In some embodiments, step 1110 includes adjusting the extant light drive parameter based on the comparison. In an example, when the comparison of step 1108 shows that the extant value of the light drive parameter is greater than the parameter limit, the parameter may be reduced. In some embodiments, the value that exceeds the limit may be updated to be equal to the limit. In some embodiments, the value may be updated to a value that is based on the old value, based on a comparison with the limit, to any other suitable value, or any combination thereof. In an example, if the light drive parameter is 40 mA and the limit determined in step 1106 is 25 mA, the system may determine to update the extant parameter to 25 mA. In another example, the light drive parameter may be halved to 20 mA and then compared to the limit again. In another example, the light drive parameter may be multiplied by a factor such as 0.8, and may be compared to the limit again. The system may determine, based on the comparison, not to update the light drive parameter. For example, if the parameter is less than the limit, the system may determine not to update the parameter.

It will be understood that a light drive parameter may be updated to a value that is less than the parameter limit. In some embodiments, the system may update light drive parameters based on received light intensity and other system parameters in addition to the comparison to the light drive parameter limit. The system may adjust light drive parameters, for example, to maximize the utilization of an analog-to-digital converter input. In some embodiments, amplification gains, current levels, and other system parameters may have fixed set point levels. That is to say, a continuous range of parameters may not be available. Additionally, drive currents and other parameters for different wavelength light emitters may be non-equal. Thus, in order to optimize the signal, the system may update a light drive parameter based on a light drive parameter limit to a value that is less that the limit.

It will be understood that in systems where multiple light drive parameter limits are maintained, multiple comparisons to multiple light drive parameters may be made by the system. It will also be understood that one or more light drive parameters may be compared and updated based on one or more light drive parameter limits, where the relative number of parameters and limits include any suitable combinations. For example, the system may compare two light drive parameters to a single light drive parameter limit, where the light drive parameters are the extant light drive currents for two light emitters (e.g., red and IR LEDs).

It will be understood that while the aforementioned examples of limits assume an upper limit, the system may use upper limits, lower limits, lower and upper limits, thresholds, bands, any other suitable limits, or any combination thereof. Comparisons to the limit and the updating will be modified accordingly. For example, where the limit is a lower limit, a light drive parameter may be increased when it falls below a lower limit.

Step 1112 includes generating a light drive signal based on the extant light drive parameter. Step 1112 may be performed by light signal generation module 410 of FIG. 4. In some embodiments, a light drive signal is generated based on the light drive parameter that may have been adjusted or updated in step 1110. In an example, where the light drive parameter is a current I, step 1112 may include generating a light drive signal with current I. In another example, where the light drive parameter is a duty cycle that has been updated in step 1110 based on a comparison made in step 1108 to a limit determined in step 1106, step 1112 may include generating a light drive signal with the updated duty cycle. In some embodiments, the generated light drive signal may be provided to a light emitter, such as light source 130 of FIG. 1.

Figure 12:
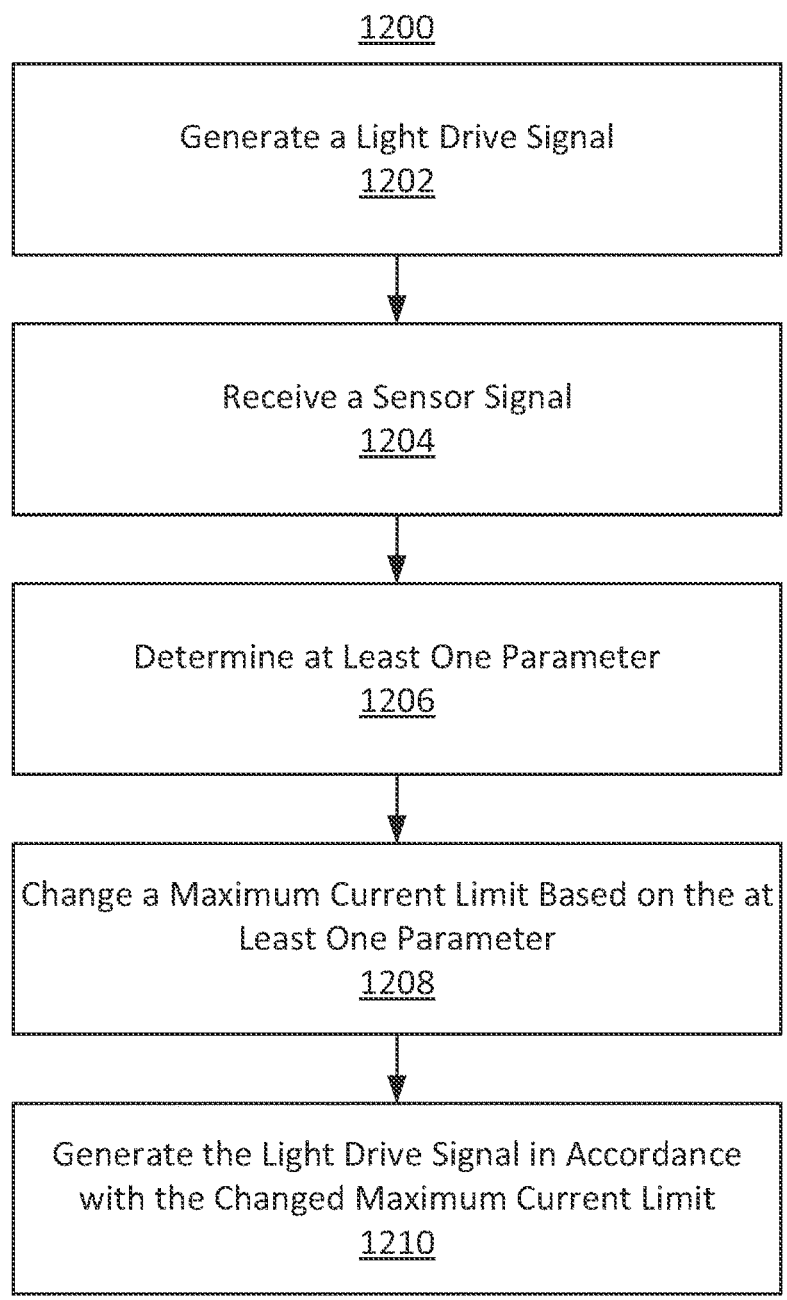
FIG. 12 shows an illustrative flow diagram including steps for generating a light drive signal in accordance with some embodiments of the present disclosure.

FIG. 12 shows illustrative flow diagram 1200 including steps for generating a light drive signal in accordance with some embodiments of the present disclosure. In some embodiments, steps of flow diagram 1200 include steps carried out by the modules illustrated in FIGS. 4-6.

Step 1202 includes generating a light drive signal. Step 1202 may be performed by light signal generation module 410 of FIG. 4. In some embodiments, a light drive signal is generated based on one or more light drive parameters. The one or more light drive parameters may include, for example, a current I and a duty cycle. It will also be understood that the light drive signal may include shaped pulses, sinusoidal modulations, time division multiplexing, frequency division multiplexing, phase division multiplexing, any other suitable light drive scheme, or any combination thereof. In some embodiments, the light drive signal may be configured to drive a light source (e.g., light source 130 of FIG. 1) of a medical sensor to emit one, two, or more wavelengths of light. FIG. 2A depicts an illustrative light drive signal that may be generated in step 1202 to drive a light source to emit two wavelengths of light.

Step 1204 includes receiving a sensor signal. A sensor signal may be received as described for parameter processing module 402 of FIG. 4. The sensor signal may include signal 506 of FIG. 5. In some embodiments, a sensor signal may be received from a medical sensor such as sensor 102 of FIG. 1. Receiving a sensor signal may include receiving an electrical and/or optical signal from a sensor. Sensors may include photodetectors that are included in a photoplethysmographic system. Sensors may additionally or alternatively include other photodetectors, ECG sensors, pulse rate sensors, blood analysis sensors, catheters, blood pressure sensors, any other suitable sensor, or any combination thereof. Sensor information may be received continuously, at regular intervals, at any other suitable time, or any combination thereof.

Step 1206 includes determining at least one parameter. The at least one parameter may be determined based on the sensor signal. In some embodiments, a single parameter may be determined. In some embodiments, two or more parameters may be determined. In some embodiments, the parameters determined by parameter processing module 402 of FIG. 4 and/or parameter processing module 502 of FIG. 5 may be determined in step 1206. In some embodiments, step 1206 may correspond to step 1104 of FIG. 11.

Step 1208 includes changing a maximum current limit based on the at least one parameter. In some embodiments, the parameter may be compared to a threshold and based on the comparison, the maximum current limit is changed. For example, when the parameter is signal strength and signal strength falls below a threshold, the maximum current limit can be increased. As another example, when the parameter is signal strength and signal strength goes above a threshold, the maximum current limit can be decreased. It will be understood that any suitable parameter and combination of parameters can be used to change the maximum current limit. In some embodiments, each of multiple parameters may be compared to a respective threshold or condition. A vote may be determined for each parameter and the votes may be combined. The maximum current limit can be changed based on the combined vote. For example, the maximum current limit can be reduced if the combined vote indicates that all of the parameters met their respective thresholds or conditions. The parameters can include physiological parameters, system parameters, signal parameters, and any combination thereof.

In addition, any of the hysteresis techniques described herein may be used in step 1208 to control when the maximum current limit is changed. In some embodiments, the maximum current limit is changed as described for light drive parameter limit decision module 404 and regulation module 406 of FIG. 4. In some embodiments, step 1208 may correspond to step 1106 of FIG. 11.

Step 1210 includes generating the light drive signal in accordance with the changed maximum current limit. Step 1210 may be performed by light signal generation module 410 of FIG. 4. The light drive signal is generated such that its current level is equal to or below the maximum current limit. In an example where the maximum current limit was increased, the current level of the light drive signal may remain the same or be increased provided that the current level is equal to or below the maximum current limit. In another example where the maximum current limit was decreased, the current level of the light drive signal may remain the same or be decreased provided that the current level is equal to or below the maximum current limit. In some embodiments, where the light drive signal is configured to drive a light source to emit two wavelengths of light, the current level associated with each wavelength may change, the current level associated with one only wavelength may change, or the current level associated with each wavelength may remain the same. In some embodiments, step 1210 may include driving a medical sensor in accordance with a reduced maximum current limit. In some embodiments, step 1210 may correspond to steps 1110 and 1112 of FIG. 11.

Figure 13:
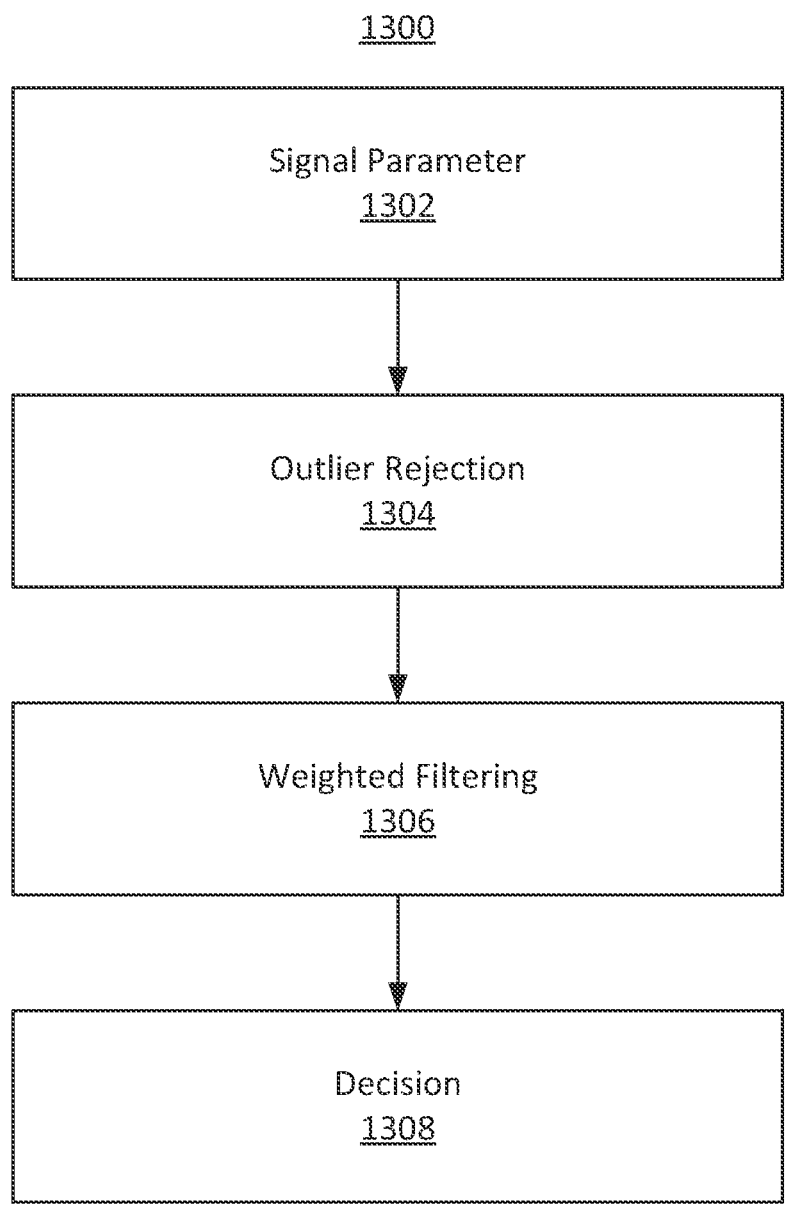
FIG. 13 shows an illustrative flow diagram including steps processing a signal in accordance with some embodiments of the present disclosure.

FIG. 13 shows illustrative flow diagram 1300 including steps for processing a signal in accordance with some embodiments of the present disclosure. Flow diagram 1300 may include steps carried out by parameter processing module 502 of FIG. 5 and light drive parameter limit decision module 504. Flow diagram 1300 includes filtering and other steps that may be applied to a determined parameter.

In step 1302, the system may determine a parameter. Determining a parameter may be performed as described for step 1104 of FIG. 11 and for step 1206 of FIG. 12.

In step 1304, the system may reject outliers. Outlier rejection may be applied to one or more parameters in order to, for example, improve parameter accuracy, reduce noise, reduce incorrect readings, for any other suitable reason, or any combination thereof. Outlier rejection may be applied to parameters individually or in any suitable combination. For example, detecting an outlier in one parameter may cause related parameters to be rejected. Outlier rejection may be implemented using statistical techniques, feedback techniques, feed forward techniques, thresholding, any other suitable technique, or any combination thereof. Thresholding may include limits set manually or automatically. For example, the system may determine reasonable limits for a parameter based on a patients age, and may reject values outside of those limits. In another example, the system may compare an extant parameter value to a moving average of the prior parameter values, and may reject values that exceed a percentage difference from the moving average. In another example, the system may reject parameters that exceed or fall below predetermined limits.

In step 1306, the system may apply filtering. Filtering may include any suitable filtering as described above in relation to parameter processing module 502 of FIG. 5. Filtering may include averaging, weighted averaging, time-dependent filtering (e.g., infinite impulse response filtering, finite impulse response filtering), adaptive filtering, any other suitable filtering, or any combination thereof. Filtering parameters may be predetermined, determined based on user input, determined based on system design, determined based on subject information, determined based on prior parameters, determined based on any other suitable information, or any combination thereof. Filtering may be applied to individual parameters or any suitable groups of parameters. Filtering need not be the same for each parameter to which filtering is applied.

In step 1308, the system may determine a decision. The decision may be determined based on the parameter determined in step 1302 and processed in steps 1304 and 1306. The decision may be determined as described in relation to the decision modules of light drive parameter limit decision module 504 of FIG. 5.

Figure 14:
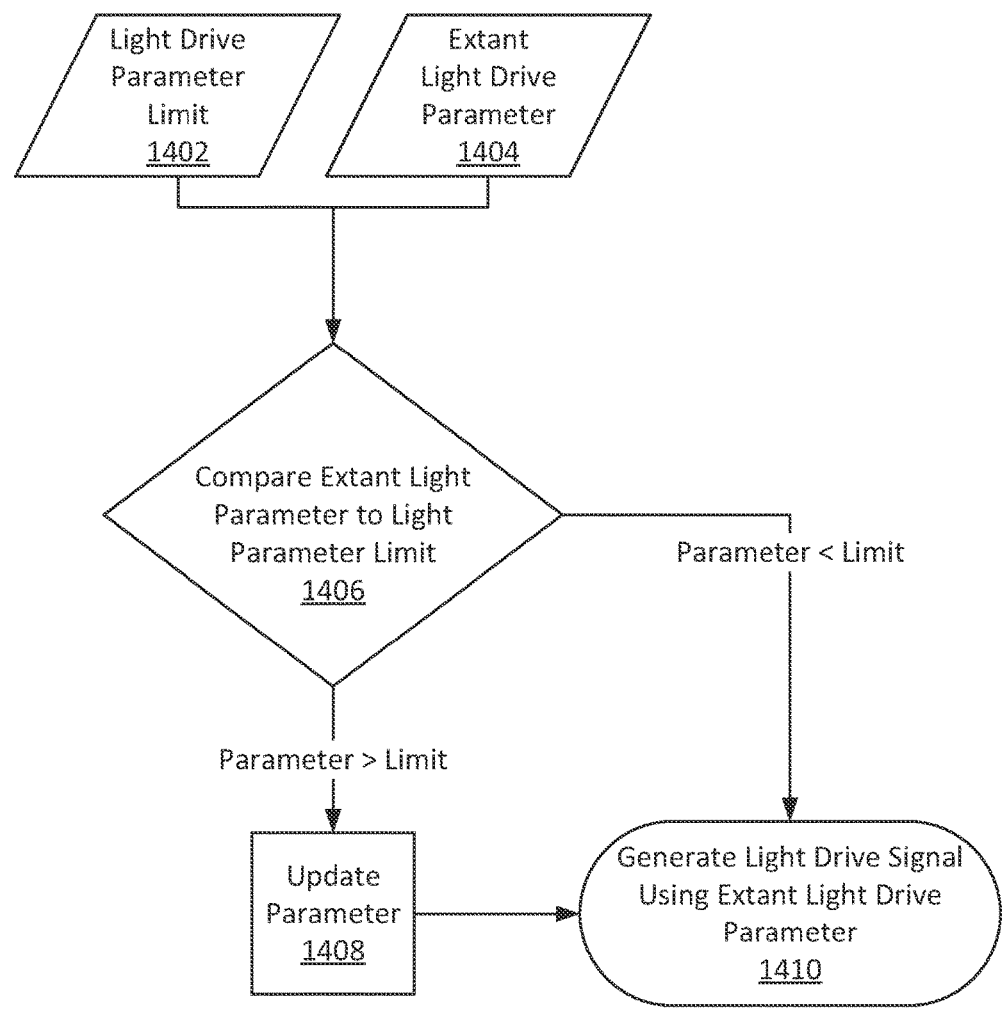
FIG. 14 shows an illustrative decision flowchart including comparing a parameter to a parameter limit in accordance with some embodiments of the present disclosure.

FIG. 14 shows illustrative decision flowchart 1400 including comparing a parameter to a parameter limit in accordance with some embodiments of the present disclosure. Flowchart 1400 may illustrate processing carried out in steps 1108, 1110, and 1112 of FIG. 11 and in steps 1208 and 1210 of FIG. 12.

Data node 1402 includes a light drive parameter limit. In some embodiments, the light drive parameter limit may have been determined in step 1106 of FIG. 11 or in step 1208 of FIG. 12. For example, the light drive parameter limit may be an $I_{max}$ value. The light drive parameter limit of data node 1402 may have been updated in step 1110 of FIG. 11.

Data node 1404 includes an extant light drive parameter. The extant light drive parameter may be the light drive parameter to which the limit is compared in step 1108 of FIG. 11. For example, the extant light drive parameter may be an electrical current value I that is being used to generate a light drive signal. In another example, the extant light drive parameter may be an extant duty cycle.

At decision node 1406, the system may compare the light drive parameter limit from data node 1402 to the extant light drive parameter from data node 1404. In the illustrated example, if the parameter is greater than the limit, the system continues to node 1408. If the parameter is less than the limit, the system continues to end point node 1410.

In node 1408, the extant parameter is updated based on the comparison. In some embodiments, the parameter may be updated to be equal to the limit. For example, if the extant parameter is 40 and the limit is 25, the parameter is updated to 25. The system then continues to end point node 1410. In some embodiments, the parameter may be updated based on the limit, based on any other suitable information, based on any other suitable technique, or any combination thereof. In an example, if the extant parameter is 40 and the limit is 25, the parameter may be divided by 2 and thus set to 20. In another example, the extant parameter may be reduced by 10% when it exceeds the limit parameter. In another example, the extant parameter may be updated to be 80% of the limit when it exceeds the limit.

In end point node 1410, the system generates a light drive signal using the light drive parameter. Where the light drive parameter has been updated in node 1408, the system uses the updated light drive parameter.

Figure 15:
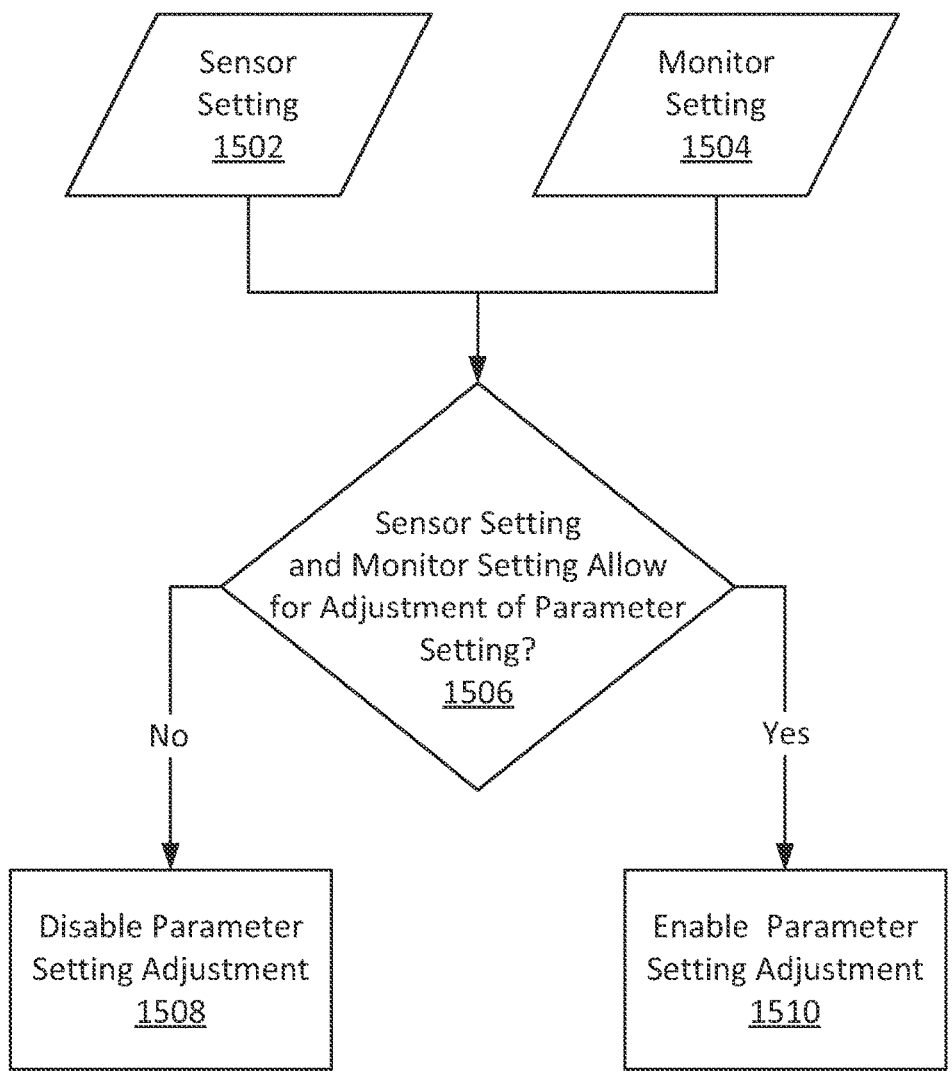
FIG. 15 shows an illustrative decision flowchart for determining whether to enable adjustment of a parameter setting in accordance with some embodiments of the present disclosure.

FIG. 15 shows illustrative decision flowchart 1500 for determining whether to enable the adjustment of a parameter setting in accordance with some embodiments of the present disclosure. For example, flowchart 1500 may be used to enable or disable light drive parameter limit decision module 404 and regulation module 406 of FIG. 4. As another example, flowchart 1500 may be used to enable or disable the adjustment of a parameter limit in flow diagram 1100 of FIG. 11 and in flow diagram 1200 of FIG. 12.

Data node 1502 of FIG. 15 includes a sensor setting. Data node 1502 may be located on a monitor such as monitor 104 of FIG. 1. In some embodiments, the sensor setting is received from a sensor (e.g., sensor 102 of FIG. 1). In some embodiments, the sensor setting is set at the monitor based on information received from the sensor. For example, the monitor may determine the sensor setting based on sensor identification information such as sensor type identification information. The sensor setting may indicate whether the sensor allows for the adjustment of a parameter setting.

Data node 1504 of FIG. 15 includes a monitor setting. Data mode 1504 may be located on a monitor such as monitor 104 of FIG. 1. In some embodiments, the monitor setting may be set to a default setting when the system is turned on or when a sensor is connected to the monitor. In some embodiments, the monitor setting may be set based on user input. For example, a user may enter or select a monitor setting using user input 182 of FIG. 1. The monitor setting may indicate whether the monitor or user allows for the adjustment of the parameter setting.

At decision node 1506, the system may determine whether the sensor setting from data node 1502 and the monitor setting from data node 1504 allow for the adjustment of the parameter setting. In the illustrated example, when both settings indicate that the adjustment of the parameter setting is allowable, the system continues to node 1510. This decision may be implemented using a logical AND operation. In another example, when at least one setting allows for the adjustment of the parameter setting, the system may continue to node 1510. In this example, the decision may be implemented using a logical OR operation. At node 1510, the system enables the parameter setting adjustment. For example, the system may enable light drive parameter limit decision module 404 and regulation module 406 of FIG. 4, the adjustment of a parameter limit in flow diagram 1100 of FIG. 11, and/or the adjustment of a parameter limit in flow diagram 1200 of FIG. 12. In some embodiments, the parameter setting adjustment is set to enabled by default. When the parameter setting adjustment is already enabled, the system may not take any action at node 1510.

Referring back to decision node 1506, when one or both settings do not allow for the adjustment of the parameter setting, the system continues to node 1508. At node 1508, the system disables the parameter setting adjustment. When the parameter setting adjustment is already disabled, the system may not take any action at node 1508.

It will be understood that the aforementioned steps of flow diagram 1100 of FIG. 11, flow diagram 1200 of FIG. 12, flow diagram 1300 of FIG. 13, decision flowchart 1400 of FIG. 14, and decision flowchart 1500 of FIG. 15 are exemplary and that in some implementations, steps may be added, removed, omitted, repeated, reordered, modified in any other suitable way, or any combination thereof.

It will be understood that in some embodiments, the system need not compare an extant parameter to a limit and instead use light drive parameter limit decision module 404 of FIG. 4 to determine a light drive parameter directly.

It will be understood that in some embodiments, flow diagram 1100 of FIG. 11, flow diagram 1200 of FIG. 12, flow diagram 1300 of FIG. 13, decision flowchart 1400 of FIG. 14, and decision flowchart 1500 of FIG. 15 may be performed in connection with continuous operation of a medical device. For example, a light drive signal may be continuously generated in accordance with a light drive parameter limit and one or more physiological parameters may be continuously determined based on the received light intensity signal. One or more parameters may also be determined based on the received light intensity signal and the light drive parameter limit may continue to be updated based on the one or more parameters.

It will be understood that the limits and parameters described herein need not be selected from two discretely defined values, and may include multiple discrete values and/or continuously variable values.

It will be understood that the techniques described herein may be used in combination with other techniques to adjust a light drive signal. For example, an additional technique to adjust light signal level based on a signal-to-noise ratio may be used to adjust the signal level, while the technique of flow diagram 1100 of FIG. 11 or flow diagram 1200 of FIG. 12 is used to determine a signal level limit.

It will be understood that the system may display status information (e.g., on display 184 of FIG. 1) related to the status of the light drive parameter limit. For example, the system may display text or a graphical element, or turn on a light, indicating the current light drive parameter limit. In some embodiments, the status information may be displayed only when the light drive parameter limit is above a threshold or below a threshold. For example, when there are two light drive parameter limit states, the system may display the status information when the system is operating in the state having the lower limit. In some embodiments, the state having the lower limit is entered because the patient is stable and because the signal levels are good. Accordingly, by displaying status information when the system is operating in this state indicates to an operator that the patient is stable and that the received signals are of high quality. The state having the lower limit may be referred to as a low power mode and the system may display status information indicating that the system is operating in a low power mode when operating in the state having the lower limit.

In some embodiments, the displayed status information may be based on historical or statistical data regarding the status of the light drive parameter limit. In one example, the system may display the percentage of time the system is operating with a particular light drive parameter limit or in a particular state. In another example, the system may display how long the system has been operating at the current light drive parameter limit or in the current state. In another example, the system may track and display information indicating how often or frequently the system toggles between limits or states. In some embodiments, the system may display a warning when the system is toggling too often. In some embodiments, the displayed status information may indicate the current power usage of the system. For example, the system may display a bar plot where the length of the bar corresponds to how much power is currently being used by the system.

It will be understood that the techniques described herein may be used for determining a parameter setting other than a light drive parameter limit. In some embodiments, the techniques described herein may be used for determining a system operating parameter setting. System operating parameter settings may include, for example, a sleep mode setting, a processor load setting, any other suitable system operating parameter setting that affects the amount of power consumed by the system, and any combination thereof. In some embodiments, the sleep mode setting may be turned on or off based on the techniques described herein. For example, when the parameters determined in parameter processing module 402 of FIG. 4 satisfy their corresponding thresholds or conditions, the sleep mode setting is turned on. In some embodiments, when the sleep mode setting is turned on, the system will alternative between its normal operating mode and a sleep mode to reduce power consumption. For example, the system may operate normally for 2 seconds to determine and display physiological parameters and then enter sleep mode for 3 seconds while continuing to display the previously determined physiological parameters. In some embodiments, the processor load setting may be determined based on the techniques described herein. For example, when the parameters determined in parameter processing module 402 of FIG. 4 satisfy their corresponding thresholds or conditions, the processor load setting may be set to a lower level. In some embodiments, the processor load setting may control how often physiological parameters are determined. In some embodiments, the processor load setting may control the clock rate of a processor. In some embodiments, the processor load setting may determine which software modules are executed by the processor. For example, the processor load setting may control whether a more computationally intensive algorithm is executed or whether a less computationally intensive algorithm is executed. In some embodiments, the techniques described herein may be used for determining one or more light drive parameter limits, one or more system operating parameter settings, or any combination thereof.

It will be understood that the aforementioned techniques are not limited to optical pulse oximetry, and may be applied to any suitable signal processing in any suitable system. For example, the techniques may be applied to electrical signals additionally or alternatively to applying it to optical signals. In another example, the techniques may be applied additionally or alternatively to respiration signals.

The foregoing is merely illustrative of the principles of this disclosure and various modifications may be made by those skilled in the art without departing from the scope of this disclosure. The above described embodiments are presented for purposes of illustration and not of limitation. The present disclosure also can take many forms other than those explicitly described herein. Accordingly, it is emphasized that this disclosure is not limited to the explicitly disclosed methods, systems, and apparatuses, but is intended to include variations to and modifications thereof, which are within the spirit of the following claims.

What is claimed:

1. A method for driving a medical sensor for use on a subject, comprising:
   generating a light drive signal with a variable current below a first maximum current limit, the light drive signal being configured to produce an emitted light in a medical sensor;
   receiving a sensor signal from the medical sensor, in response to the emitted light;
   determining a parameter based on the received sensor signal;
   changing the maximum current limit based on the parameter; and
   generating the light drive signal in accordance with the changed maximum current limit.

2. The method of claim 1, wherein generating the light drive signal in accordance with the changed maximum current limit comprises changing a level of current of the light drive signal.

3. The method of claim 1, wherein the parameter comprises a physiological parameter, a system parameter, or a signal quality parameter.

4. The method of claim 1, wherein the parameter comprises a first parameter, the method further comprising:
   determining a second parameter;
   making a first decision based on the first parameter;
   making a second decision based on the second parameter; and
   combining the first decision and the second decision, wherein:
   changing the maximum current limit comprises changing the maximum current limit based on the combination of the first decision and the second decision.

5. The method of claim 4, wherein combining comprises a logical AND operation.

6. The method of claim 1, wherein changing the maximum current limit comprises using a state machine based at least in part on the parameter.

7. The method of claim 6, wherein the state machine comprises hysteresis.

8. The method of claim 1, wherein changing the maximum current limit comprises applying hysteresis.

9. The method of claim 1, wherein changing the maximum current limit comprises comparing the parameter to a threshold.

10. The method of claim 1, wherein the parameter is selected from the group consisting of percent modulation, nAv, oxygen saturation, pulse rate, signal quality, a variability of a physiological parameter, and combinations thereof.

11. The method of claim 1, further comprising:
    determining a physiological parameter of the subject based at least in part on the received sensor signal.

12. The method of claim 1, wherein generating the light drive signal in accordance with the maximum current limit comprises generating the light drive signal at a first current, wherein generating the light drive signal in accordance with the changed maximum current limit comprises generating the light drive signal at a second current, and wherein the second current is less than the first current.

13. The method of claim 1, wherein generating the light drive signal with a variable current below a first maximum current limit comprises generating the light drive signal at a first current, wherein generating the light drive signal in accordance with the changed maximum current limit comprises generating the light drive signal at a second current, and wherein the second current is greater than the first current.

14. The method of claim 1, wherein generating the light drive signal with a variable current below a first maximum current limit comprises generating the light drive signal at a first current, and wherein generating the light drive signal in accordance with the changed maximum current limit comprises generating the light drive signal at the same first current.

15. The method of claim 1, wherein changing the maximum current limit based on the parameter comprises changing the maximum current limit if the parameter exceeds a threshold for a duration of time.

16. The method of claim 1, wherein the medical sensor comprises a pulse oximetry sensor having first and second light emitters, wherein generating the light drive signal with a variable current below a first maximum current limit comprises generating first and second light drive signals for producing emitted light from the first and second light emitters, respectively, and wherein generating the light drive signal in accordance with the changed maximum current limit comprises generating the first and second light drive signals in accordance with the changed maximum current limit.

17. The method of claim 16, wherein generating the first and second light drive signals in accordance with the changed maximum current limit comprises changing a current of one but not both of the first and the second light drive signals.

18. The method of claim 1, wherein generating the light drive signal in accordance with the changed maximum current limit comprises varying a current level of the light drive signal, while remaining below or equal to the maximum current limit.

19. A method for monitoring a physiological parameter of a subject, comprising:
   driving a medical sensor with a varying current below a first maximum current to emit light into a subject;
   receiving a sensor signal from the medical sensor in response to the emitted light;
   determining a plurality of parameters based on the sensor signal;
   comparing each of the plurality of parameters to a respective threshold or condition;
   determining, for each of the plurality of parameters, a vote based on whether the parameter meets its respective threshold or condition;
   combining the votes of the plurality of parameters;
   reducing the maximum current limit available to the medical sensor based on the combined votes; and
   driving the medical sensor with varying current below the reduced maximum current limit.

20. The method of claim 19, wherein combining the votes of the plurality of parameters comprises a logical AND operation.

21. The method of claim 19, wherein reducing the maximum current limit available comprises reducing the maximum current if the combined vote is affirmative for a minimum duration of time.

22. The method of claim 19, further comprising increasing the maximum current limit available to the medical sensor if the combined vote is negative for a minimum duration of time.

* * * * *